United States Patent
Bearss et al.

(10) Patent No.: US 10,835,537 B2
(45) Date of Patent: *Nov. 17, 2020

(54) COMBINATION THERAPIES FOR TREATMENT OF CANCER

(71) Applicant: Sumitomo Dainippon Pharma Oncology, Inc., Cambridge, MA (US)

(72) Inventors: David J. Bearss, Lehi, UT (US);
Steven L. Warner, Lehi, UT (US);
Adam Siddiqui-Jain, Lehi, UT (US);
Clifford J. Whatcott, Lehi, UT (US);
Wontak Kim, Lehi, UT (US)

(73) Assignee: Sumitomo Dainippon Pharma Oncology, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/821,762

(22) Filed: Mar. 17, 2020

(65) Prior Publication Data
US 2020/0215071 A1 Jul. 9, 2020

Related U.S. Application Data

(63) Continuation of application No. 16/665,277, filed on Oct. 28, 2019, now Pat. No. 10,682,356, which is a continuation of application No. 15/750,151, filed as application No. PCT/US2016/045423 on Aug. 3, 2016, now Pat. No. 10,568,887.

(60) Provisional application No. 62/200,499, filed on Aug. 3, 2015.

(51) Int. Cl.
| | |
|---|---|
| *A61K 31/453* | (2006.01) |
| *A61K 31/519* | (2006.01) |
| *A61K 31/706* | (2006.01) |
| *A61K 31/4433* | (2006.01) |
| *A61K 45/06* | (2006.01) |
| *A61P 35/02* | (2006.01) |
| *A61K 31/445* | (2006.01) |
| *C07D 405/04* | (2006.01) |
| *C07D 405/10* | (2006.01) |

(52) U.S. Cl.
CPC .......... *A61K 31/519* (2013.01); *A61K 31/445* (2013.01); *A61K 31/4433* (2013.01); *A61K 31/453* (2013.01); *A61K 31/706* (2013.01); *A61K 45/06* (2013.01); *A61P 35/02* (2018.01); *C07D 405/04* (2013.01); *C07D 405/10* (2013.01); *A61K 2300/00* (2013.01)

(58) Field of Classification Search
None
See application file for complete search history.

(56) References Cited

U.S. PATENT DOCUMENTS

| | | |
|---|---|---|
| 4,132,710 A | 1/1979 | Gauthier et al. |
| 4,522,811 A | 6/1985 | Eppstein et al. |
| 4,676,980 A | 6/1987 | Segal et al. |
| 4,816,567 A | 3/1989 | Cabilly et al. |
| 4,900,727 A | 2/1990 | Kattige et al. |
| 4,946,778 A | 8/1990 | Ladner et al. |
| 4,971,909 A | 11/1990 | Kaneoya et al. |
| 5,225,539 A | 7/1993 | Winter |
| 5,284,856 A | 2/1994 | Naik et al. |
| 5,310,763 A | 5/1994 | Campion et al. |
| 5,545,806 A | 8/1996 | Lonberg et al. |
| 5,545,807 A | 8/1996 | Surani et al. |
| 5,569,825 A | 10/1996 | Lonberg et al. |
| 5,587,458 A | 12/1996 | King et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,674,980 A | 10/1997 | Frankel et al. |
| 5,747,498 A | 5/1998 | Schnur et al. |
| 5,792,783 A | 8/1998 | Tang et al. |
| 5,804,604 A | 9/1998 | Frankel et al. |
| 5,834,504 A | 11/1998 | Tang et al. |
| 5,849,733 A | 12/1998 | Kim |
| 5,861,510 A | 1/1999 | Piscopio et al. |
| 5,863,949 A | 1/1999 | Robinson et al. |
| 5,877,305 A | 3/1999 | Huston et al. |
| 5,883,113 A | 3/1999 | Tang et al. |
| 5,886,020 A | 3/1999 | Tang et al. |
| 5,908,934 A | 6/1999 | Kim |
| 5,916,771 A | 6/1999 | Hori et al. |
| 5,932,595 A | 8/1999 | Bender et al. |
| 5,939,598 A | 8/1999 | Kucherlapati et al. |
| 5,965,703 A | 10/1999 | Horne et al. |
| 6,077,864 A | 6/2000 | Burgess et al. |

(Continued)

FOREIGN PATENT DOCUMENTS

| | | |
|---|---|---|
| CN | 1583776 A | 2/2005 |
| CN | 105919955 A | 6/2016 |

(Continued)

OTHER PUBLICATIONS

Karp et al., "Timed Sequential Therapy of Acute Leukemia with Flavopiridol: In Vitro Model fora Phase I Clinical Trial" Clinical Cancer Research vol. 9 pp. 307-315 (Year: 2003).*

Raychaudhuri, "Low probability Bid-Bax reaction generates heterogeneity in apoptosis resistance of cancer and cancer stem cells," arXiv:1108.2091 [q-bio.MN], 2011, 17 pages.

Ren et al., "BID, BIM, and PUMA Are Essential for Activation of the BAX- and BAK-Dependent Cell Death Program," *Science* 330:1390-1393, 2010.

Rezaei et al., "Leukemia markers expression of peripheral blood vs. bone marrow blasts using flow cytometry," *Med Sci. Monit* 9:CR359-CR362 with cover page, 2003.

(Continued)

*Primary Examiner* — Eric Olson
(74) *Attorney, Agent, or Firm* — Oblon, McClelland, Maier & Neustadt, L.L.P.

(57) ABSTRACT

Combination therapies for treatment of cancer are provided. The disclosed methods comprise administration of a cyclin-dependent kinase inhibitor and a DNA methyltransferase inhibitor to a mammal in need thereof.

6 Claims, 6 Drawing Sheets

(56) References Cited

U.S. PATENT DOCUMENTS

| | | |
|---|---|---|
| 6,087,366 A | 7/2000 | Park et al. |
| 6,087,392 A | 7/2000 | Reiter |
| 6,090,852 A | 7/2000 | Dack et al. |
| 6,110,964 A | 8/2000 | Robinson |
| 6,136,981 A | 10/2000 | Brion et al. |
| 6,147,061 A | 11/2000 | Reiter |
| 6,153,609 A | 11/2000 | Robinson et al. |
| 6,177,401 B1 | 1/2001 | Ullrich et al. |
| 6,207,669 B1 | 3/2001 | Cockerill et al. |
| 6,214,872 B1 | 4/2001 | Robinson |
| 6,225,473 B1 | 5/2001 | Breipohl et al. |
| 6,258,540 B1 | 7/2001 | Lo et al. |
| 6,284,764 B1 | 9/2001 | Kath et al. |
| 6,291,455 B1 | 9/2001 | Thomas et al. |
| 6,294,532 B1 | 9/2001 | Thomas et al. |
| 6,303,636 B1 | 10/2001 | Robinson, Jr. et al. |
| 6,362,336 B1 | 3/2002 | Lohmann et al. |
| 6,406,912 B1 | 6/2002 | Holla |
| 6,437,136 B2 | 8/2002 | Breipohl et al. |
| 6,492,383 B1 | 12/2002 | Munchhof et al. |
| 6,495,568 B1 | 12/2002 | Dack et al. |
| 6,511,993 B1 | 1/2003 | Dack et al. |
| 6,576,647 B2 | 6/2003 | Bafus et al. |
| 6,587,123 B2 | 7/2003 | Ando et al. |
| 6,596,726 B1 | 7/2003 | Bridges et al. |
| 6,599,890 B1 | 7/2003 | McClure et al. |
| 6,723,726 B1 | 4/2004 | Cockerill et al. |
| 6,821,990 B2 | 11/2004 | Kesseler |
| 6,828,320 B2 | 12/2004 | Cockerill et al. |
| 6,849,631 B2 | 2/2005 | Carini |
| 7,064,193 B1 | 6/2006 | Coly et al. |
| 7,119,090 B2 | 10/2006 | Tang et al. |
| 7,417,055 B2 | 8/2008 | Cannizzaro |
| 7,452,901 B2 | 11/2008 | Boojamra et al. |
| 7,572,924 B2 | 8/2009 | Tang et al. |
| 7,714,005 B2 | 5/2010 | Chen et al. |
| 7,790,902 B2 | 9/2010 | Larson et al. |
| 7,829,662 B2 | 11/2010 | Korsmeyer et al. |
| 7,868,133 B2 | 1/2011 | Korsmeyer et al. |
| 8,168,755 B2 | 5/2012 | Cardone et al. |
| 8,221,966 B2 | 7/2012 | Letai |
| 8,372,819 B2 | 2/2013 | Jones et al. |
| 8,758,752 B2 | 6/2014 | Govindan et al. |
| 8,822,526 B2 | 9/2014 | Rathos et al. |
| 8,975,239 B2 | 3/2015 | Green et al. |
| 9,138,485 B2 | 9/2015 | Govindan et al. |
| 9,199,973 B2 | 12/2015 | Carter et al. |
| 9,241,941 B2 | 1/2016 | Wendal et al. |
| 9,340,524 B2 | 5/2016 | Chen et al. |
| 9,360,473 B2 | 6/2016 | Cardone |
| 9,493,454 B2 | 11/2016 | Zeng et al. |
| 9,540,674 B2 | 1/2017 | Letai |
| 9,758,539 B2 | 9/2017 | Siddiqui-Jain et al. |
| 9,856,303 B2 | 1/2018 | Korsmeyer et al. |
| 9,901,574 B2 | 2/2018 | Warner et al. |
| 9,902,759 B2 | 2/2018 | Korsmeyer et al. |
| 9,925,192 B2 | 3/2018 | Strack et al. |
| 10,132,797 B2 | 11/2018 | Bearss et al. |
| 10,259,835 B2 | 4/2019 | Siddiqui-Jain et al. |
| 10,267,787 B2 | 4/2019 | Bearss et al. |
| 10,357,488 B2 | 7/2019 | Warner et al. |
| 10,422,788 B2 | 9/2019 | Bearss et al. |
| 10,562,925 B2 | 2/2020 | Siddiqui-Jain et al. |
| 10,568,887 B2 * | 2/2020 | Bearss ............... A61K 31/4433 |
| 2002/0016293 A1 | 2/2002 | Ratain et al. |
| 2002/0115613 A1 | 8/2002 | Kumar |
| 2002/0177609 A1 | 11/2002 | Swindell et al. |
| 2003/0065023 A1 | 4/2003 | Swindell et al. |
| 2003/0073661 A1 | 4/2003 | Matsuyama et al. |
| 2004/0106647 A1 | 6/2004 | Schneider et al. |
| 2004/0171809 A1 | 9/2004 | Korsmeyer et al. |
| 2005/0153991 A1 | 7/2005 | Gianella-Borradori et al. |
| 2007/0093490 A1 | 4/2007 | Prien et al. |
| 2008/0027105 A1 | 1/2008 | Suarez et al. |
| 2009/0030005 A1 | 1/2009 | Kamb et al. |
| 2009/0142337 A1 | 6/2009 | Squires |
| 2010/0143350 A1 | 6/2010 | Green et al. |
| 2010/0286057 A1 | 11/2010 | Walensky et al. |
| 2011/0008371 A1 | 1/2011 | Michelson |
| 2011/0251240 A1 | 10/2011 | Suarez et al. |
| 2012/0225851 A1 | 9/2012 | Cardone et al. |
| 2013/0079424 A1 | 3/2013 | Gerber et al. |
| 2013/0122492 A1 | 5/2013 | Khosravi et al. |
| 2013/0210024 A1 | 8/2013 | Yu et al. |
| 2014/0113919 A1 | 4/2014 | Baffert et al. |
| 2014/0286861 A1 | 9/2014 | Govindan et al. |
| 2014/0303167 A1 | 10/2014 | Choidas et al. |
| 2015/0051249 A1 | 2/2015 | Walensky |
| 2015/0150869 A1 | 6/2015 | Cardone et al. |
| 2015/0301053 A1 | 10/2015 | Pierceall et al. |
| 2015/0352097 A1 | 12/2015 | Cardone et al. |
| 2015/0362479 A1 | 12/2015 | Letai et al. |
| 2016/0178612 A1 | 6/2016 | Cardone |
| 2016/0200786 A1 | 7/2016 | Korsmeyer et al. |
| 2016/0231314 A1 | 8/2016 | Ryan et al. |
| 2016/0235779 A1 | 8/2016 | Marcus |
| 2016/0258933 A1 | 9/2016 | Letai |
| 2016/0273020 A1 | 9/2016 | Pierceall et al. |
| 2016/0279106 A1 | 9/2016 | Udea et al. |
| 2016/0340376 A1 | 11/2016 | Siddiqui-Jain et al. |
| 2017/0184567 A1 | 6/2017 | Letai |
| 2017/0260268 A1 | 9/2017 | Beatty et al. |
| 2018/0256580 A1 | 9/2018 | Bearss |
| 2018/0280407 A1 | 10/2018 | Warner et al. |
| 2019/0030017 A1 | 1/2019 | Warner et al. |
| 2019/0177350 A1 | 6/2019 | Siddiqui-Jain et al. |
| 2019/0314357 A1 | 10/2019 | Bearss et al. |
| 2020/0054642 A1 * | 2/2020 | Bearss ................ A61K 31/706 |

FOREIGN PATENT DOCUMENTS

| | | |
|---|---|---|
| EP | 0507278 A2 | 10/1992 |
| EP | 0241003 B1 | 10/1993 |
| EP | 0321918 B1 | 3/1994 |
| EP | 0366061 B1 | 1/1996 |
| EP | 0474129 B1 | 12/1996 |
| EP | 0 780 386 A1 | 6/1997 |
| EP | 0606046 B1 | 10/1997 |
| EP | 0818442 A2 | 1/1998 |
| EP | 0 931 788 A2 | 7/1999 |
| EP | 1004578 A2 | 5/2000 |
| EP | 0979824 B1 | 10/2004 |
| EP | 3049443 A4 | 8/2016 |
| FR | 2338043 A1 | 8/1977 |
| IN | CHENP200703645 | 11/2007 |
| RU | 2009146008 A | 6/2011 |
| RU | 2474582 C2 | 10/2013 |
| RU | 2552642 C2 | 10/2015 |
| WO | 90/05719 A1 | 5/1990 |
| WO | 91/00360 A1 | 1/1991 |
| WO | 92/20373 A1 | 11/1992 |
| WO | 93/08829 A1 | 5/1993 |
| WO | 94/02602 A1 | 2/1994 |
| WO | 94/11026 A2 | 5/1994 |
| WO | 95/19970 A1 | 7/1995 |
| WO | 95/21613 A1 | 8/1995 |
| WO | 96/15263 A1 | 5/1996 |
| WO | 96/27011 A1 | 9/1996 |
| WO | 96/27583 A1 | 9/1996 |
| WO | 96/33172 A1 | 10/1996 |
| WO | 96/33735 A1 | 10/1996 |
| WO | 96/34096 A1 | 10/1996 |
| WO | 97/05265 A1 | 2/1997 |
| WO | 97/13760 A1 | 4/1997 |
| WO | 1997/16447 A1 | 5/1997 |
| WO | 97/22596 A1 | 6/1997 |
| WO | 1997/30174 A1 | 8/1997 |
| WO | 97/32856 A1 | 9/1997 |
| WO | 1997/42949 A1 | 11/1997 |
| WO | 98/02434 A1 | 1/1998 |
| WO | 98/02437 A1 | 1/1998 |
| WO | 98/02438 A1 | 1/1998 |
| WO | 98/03516 A1 | 1/1998 |
| WO | 98/07697 A1 | 2/1998 |

(56) References Cited

FOREIGN PATENT DOCUMENTS

| | | |
|---|---|---|
| WO | 98/14451 A1 | 4/1998 |
| WO | 1998/13344 A1 | 4/1998 |
| WO | 98/30566 A1 | 7/1998 |
| WO | 98/33768 A1 | 8/1998 |
| WO | 98/34915 A1 | 8/1998 |
| WO | 98/34918 A1 | 8/1998 |
| WO | 1998/33798 A1 | 8/1998 |
| WO | 98/50356 A1 | 11/1998 |
| WO | 98/54093 A1 | 12/1998 |
| WO | 99/07675 A1 | 2/1999 |
| WO | 99/10349 A1 | 3/1999 |
| WO | 99/16755 A1 | 4/1999 |
| WO | 99/16787 A1 | 4/1999 |
| WO | 99/24440 A1 | 5/1999 |
| WO | 99/29667 A1 | 6/1999 |
| WO | 99/35132 A1 | 7/1999 |
| WO | 99/35146 A1 | 7/1999 |
| WO | 99/52889 A1 | 10/1999 |
| WO | 99/52910 A1 | 10/1999 |
| WO | 99/53049 A1 | 10/1999 |
| WO | 99/61422 A1 | 12/1999 |
| WO | 99/62890 A1 | 12/1999 |
| WO | 2000/06134 A2 | 2/2000 |
| WO | 2000/12071 A2 | 3/2000 |
| WO | 2000/44362 A2 | 8/2000 |
| WO | 00/59526 A1 | 10/2000 |
| WO | 01/12661 A2 | 2/2001 |
| WO | 01/60814 A2 | 8/2001 |
| WO | 02/20568 A2 | 3/2002 |
| WO | 03/028001 A1 | 4/2003 |
| WO | 03/040168 A2 | 5/2003 |
| WO | 2004/022580 A2 | 3/2004 |
| WO | 2004/058804 A1 | 7/2004 |
| WO | 2005/017107 A2 | 2/2005 |
| WO | 2005/044839 A2 | 5/2005 |
| WO | 2006/099667 A1 | 9/2006 |
| WO | 2006/101846 A1 | 9/2006 |
| WO | 2007/123791 A2 | 11/2007 |
| WO | 2008/021484 A1 | 2/2008 |
| WO | 2008/106635 A1 | 9/2008 |
| WO | 2010/093742 A1 | 8/2010 |
| WO | 2010/147961 A1 | 12/2010 |
| WO | 2011/088137 A2 | 7/2011 |
| WO | 2011/143660 A2 | 11/2011 |
| WO | 2012/122370 A2 | 9/2012 |
| WO | 2013/082660 A1 | 6/2013 |
| WO | 2013/138702 A2 | 9/2013 |
| WO | 2013/170176 A2 | 11/2013 |
| WO | 2013/170176 A3 | 11/2013 |
| WO | 2013/182519 A1 | 12/2013 |
| WO | 2013/188355 A1 | 12/2013 |
| WO | 2013/188978 A1 | 12/2013 |
| WO | 2014/047342 A1 | 3/2014 |
| WO | 2014/059028 A1 | 4/2014 |
| WO | 2014/066848 A1 | 5/2014 |
| WO | 2015/010094 A1 | 1/2015 |
| WO | 2015/017788 A1 | 2/2015 |
| WO | 2015/042249 A1 | 3/2015 |
| WO | 2015/047510 A1 | 4/2015 |
| WO | 2015/066305 A1 | 5/2015 |
| WO | 2015/070020 A2 | 5/2015 |
| WO | 2015/130585 A1 | 9/2015 |
| WO | 2015/161247 A1 | 10/2015 |
| WO | 2016/061144 A1 | 4/2016 |
| WO | 2016/073913 A1 | 5/2016 |
| WO | 2016/115105 A1 | 7/2016 |
| WO | 2016/149613 A2 | 9/2016 |
| WO | 2016/154380 A1 | 9/2016 |
| WO | 2016/161248 A1 | 10/2016 |
| WO | 2016/172214 A1 | 10/2016 |
| WO | 2016/176288 A1 | 11/2016 |
| WO | 2016/176299 A1 | 11/2016 |
| WO | 2016/187316 A1 | 11/2016 |
| WO | 2017/024073 A1 | 2/2017 |
| WO | 2017/075349 A2 | 5/2017 |
| WO | 2018/13918 A2 | 1/2018 |
| WO | 2018/094275 A1 | 5/2018 |
| WO | 2018/119000 A1 | 6/2018 |
| WO | 2019/055579 A1 | 3/2019 |
| WO | 2019/200243 A1 | 10/2019 |
| WO | 2019/246421 A1 | 12/2019 |

OTHER PUBLICATIONS

Richon et al., "A class of hybrid polar inducers of transformed cell differentiation inhibits histone deacetylases," *Proc. Natl. Acad. Sci. USA* 95:3003-3007, 1998.

Riechmann et al., "Reshaping human antibodies for therapy," *Nature* 332:323-327, 1988.

Rollins-Raval et al., "The value of immunohistochemistry for CD14, CD123, CD33, myeloperoxidase and CD68R in the diagnosis of acute and chronic myelomonocytic leukaemias," *Histopathology* 60:933-942, 2012.

Rothbard et al., "Conjugation of arginine oligomers to cyclosporine A facilitates topical delivery and inhibition of inflammation," *Nat. Med.* 6(11):1253-1257, 2000.

Rudek et al., "Clinical Pharmacology of Flavopiridol Following a 72-Hour Continuous Infusion," *Ann Pharmacother* 37:1369-1374, 2003.

Ryan et al., "Heightened mitochondrial priming is the basis for apoptotic hypersensitivity of CD4+ CD8+ thymocytes," *Proc. Natl. Acad. Sci USA* 107(29):12895-12900, 2010.

Ryan et al., "BH3 Profiling in Whole Cells by Fluorimeter or FACS," *Methods* 61:156-164, 2013. (22 pages).

Saito et al., "A synthetic inhibitor of histone deacetylase, MS-27-275, with marked in vivo antitumor activity against human tumors," *Proc. Natl. Acad. Sci. USA* 96:4592-4597, 1999.

Samson et al., "A 35 amino acid fragment of leptin inhibits feeding in the rat," *Endocrinology* 137:5182-5185, 1996.

Sattler et al., "Structure of Bxl-xl-Bak Peptide Complex: Recognition Between Regulators of Apoptosis," *Science* 275:983-986, 1997.

Sausville et al., "Inhibition of CDKs as a Therapeutic Modality," *Ann NY Acad of Sci* 910:207-222, 2000.

Schimmer et al., "The BH3 domain of BAD fused to the Antennapedia peptide induces apoptosis via its alpha helical structure and independent of Bcl-2," *Cell Death and Differentiation* 8:725-733, 2001.

Schwartz et al., "Phase II Study of the Cyclin-Dependent Kinase Inhibitor Flavopiridol Administered to Patients With Advanced Gastric Carcinoma," *J. Clin. Onc.* 19:1985-1992, 2001.

Score Search Results Details for Application 11789557 and Search Result 20091106_104627_ . . . , downloaded from URL: http://es/ScoreAccessWeb/GetItem.action?AppID=11789557swqId=09323b6780cf451a&ItemN . . . , on Nov. 24, 2009—4 pages.

Scal et al., "Identification of a novel series of BET family bromodomain inhibitors: binding mode and profile of I-BET151 (GSK1210151A)," *Bioorg. Med. Chem. Lett* 22:2968-2972, 2012.

Sedlacek et al., "Flavopiridol (L86 8275; NSC 649890), a new kinase inhibitor for tumor therapy," *International Journal of Oncology* 9:1143-1168, 1996.

Sen et al., "Artemisinin triggers induction of cell-cycle arrest and apoptosis in Leishmania donovani promastigotes," *J Med Microbiol* 56(Pt. 9):1213-1218, 2007.

Senderowicz et al., "Phase I Trial of Continuous Infusion Flavopiridol, a Novel Cyclin-Dependent Kinase Inhibitor, in Patients with Refractory Neoplasms," *J. Clin Onc* 16:2986-2999, 1998.

Senderowicz et al., "Preclinical and Clinical Development of Cyclin-Dependent Kinase Modulators," *J Natl Cancer Inst* 92:376-387, 2000.

Senderowicz, "Flavopiridol: the first cyclin-dependent kinase inhibitor in human clinical trials," *Investigational New Drugs* 17:313-320, 1999.

Score, "Search Results Details for Application 11789557 and Search Result 20091106_104627_ . . . ," Nov. 24, 2009, URL=http://es/ScoreAccessWeb/GetItem.action?AppId=11789557&seqId=09323b6780cf451a&ItemN . . . , 4 pages.

Shalaby et al., "Development of humanized bispecific antibodies reactive with cytotoxic lymphocytes and tumor cells overexpressing the HER2 protooncogene," *Exp. Med.* 175:217-225, 1992.

(56) References Cited

OTHER PUBLICATIONS

Shangary et al., "Peptides derived from BH3 domains of Bcl-2 family members: a comparative analysis of inhibition of Bcl-2, Bcl-x(L) and Bax oligomerization, induction of cytochrome c release, and activation of cell death," *Biochemistry* 41:9485-9495, 2002.

Shapiro et al., "A Phase II Trial of the Cyclin-dependent Kinase Inhibitor Flavopiridol in Patients with Previously Untreated Stage IV Non-Small Cell Lung Cancer," *Clinical Cancer Research* 7:1590-1599 with cover page, 2001.

Shibue et al., "Differential contribution of Puma and Noxa in dual regulation of p53-mediated apoptotic pathways," *The EMBO Journal* 25:4952-4962, 2006.

Shimizu et al., "Proapoptotic BH3-only Bcl-2 family members induce cytochrome c release, but not mitochondrial membrane potential loss, and do not directly modulate voltage-dependent anion channel activity," *PNAS* 97:577-582, 2000.

Shopes, "A genetically engineered human IgG mutant with enhanced cytolytic activity," *J. Immunol* 148:2918-2922, 1992.

Sinicrope et al., "Proapoptotic Bad and Bid Protein Expression Predict Survival in Stages II and III Colon Cancers," *Clin. Canc. Res.* 14(13):4128-4133, 2008.

Sinicrope et al., "Prognostic Impact of Bim, Puma, and Noxa Expression in Human Colon Carcinomas," *Clin. Canc. Res.* 14(18):5810-5818, 2008.

Smith et al., "An alvocidib-containing regimen is highly effective in AML patients through a mechanism dependent on MCL1 expression and function," *2015 ASCO Annual Meeting*, Abstract No. 7062, 2015. (3 pages).

Smith et al., "Enhancer biology and enhanceropathies," *Nature Structural & Molecular Biology* 21:210-219, 2014.

Soltow et al., "Overexpression of CuZnSOD or MnSOD protects satellite cells from doxorubicin-induced apoptosis," *FASEB J* 21:A449, 2007—Abstract.

Song et al., "Carbon monozide promotes Fas/CD95-induced apoptosis in Jurkat cells," *J. Biol Chem* 279(43):44327-44334, 2004. Erratum in: *J Biol Chem* 280(23):22555, 2005.

Song et al., "Carbon Monoxide Promotes Fas/CD95-induced Apoptosis in Jurkat Cells," *The Journal of Biological Chemistry* 279(43):44327-44334, 2004—"Additions and Correction," *The Journal of Biological Chemistry* 280(23):22555-22556, 2005. (3 pages).

Stevenson et al., "A chimeric antibody with dual Fc regions (bisFabFc) prepared by manipulations at IgG hinge," *Anti-Cancer Drug Design* 3:219-230, 1989.

Stewart et al., "The MCL-1 BH3 Helix is an Exclusive MCL-1 inhibitor and Apoptosis Sensitizer," *Nal. Chem. Biol.* 6(8):595-601, 2010. (17 pages).

Sturm et al., "Mutation of p53 and consecutive selective drug resistance in B-CLL occurs as a consequence of prior DNA-damaging chemotherapy," *Cell Death and Differentiation* 10:477-484, 2003.

Sugiyama et al., "Activation of mitochondrial voltage-dependent anion channel by a pro-apoptotic BH3-only protein Bim," *Oncogene* 21(32):4944-4956, 2002.

Suzuki et al., "Possible Existence of Common Internalization Mechanisms among Arginine-rich Peptides," *J. Biol Chem* 277:2437-2443, 2002.

Tahir et al., "Potential mechanisms of resistance to venetoclax and strategies to circumvent it," *BMC Cancer* 17:399, 2017. (10 pages).

Tan et al., "Phase I Clinical and Parmacokinetic Study of Flavopiridol Administered as a Daily 1-Hour Infusion in Patients with Advanced Neoplasms," *J Clin Oncol* 20:4074-4082, 2002.

Taussig et al., "Anti-CD38 antibody-mediated clearance of human repopulating cells masks the heterogeneity of leukemia-initiating cells," *Blood* 112(3):568-575, 2008.

Terradillos et al., "Direct addition of BimL to mitochondria does not lead to cytochrome c release," *FEBS Lett* 522(1-3):29-34, 2002.

Theisen et al., "Reversible inhibition of lysine specific demethylase 1 is a novel anti-tumor strategy for poorly differentiated endometrial carcinoma," *BMC Cancer* 14:752, 2014.

Thomas et al., "Phase I clinical and pharmacokinetic trial of the cyclin-dependent kinase inhibitor flavopiridol," *Cancer Chemother Pharmacol* 50:465-472, 2002.

Thomenius et al., "Using BH3 Profiling as a Predictive Indicator for Myeloma Patient Response to Bortezomib," *Blood* 118(21): Abstract No. 3952, 2011.

Thornton et al., "Characterisation of TP53 abnormalities in chronic lymphocytic leukaemia," *The Hematology Journal* 5:47-54, 2004.

Thornton et al., "High dose methyl prednisolone can induce remissions in CLL patients with p53 abnormalities," *Ann Hematol* 82:759-765, 2003.

Tolero Pharmaceuticals, "Jefferies 2016 Healthcare Conference," 2016, 31 pages.

Toogood et al., "Discovery of a Potent and Selective Inhibitor of Cyclin-Dependent Kinase 4/6," *J. Med. Chem.* 48:2388-2406, 2005.

Touzeau et al., "BH3 profiling identifies heterogeneous dependency on Bcl-2 family members in multiple myeloma and predicts sensitivity to BH3 mimetics," *Leukemia* 30:761-764, 2016.

Traunecker et al., "Bispecific single chain molecules (Janusins) target cytotoxic lymphocytes on HIV infected cells," *EMBO J* 10:3655-3659, 1991. (8 pages).

Tsao et al., "Concomitant inhibition of DNA methyltransferase and BCL-2 protein function synergistically induce mitochondrial apoptosis in acute myelogenous leukemia cells," *Ann Hemaltol* 91(12):1861-1870, 2012.

Tutt et al., "Trispecific F(ab')3 derivatives that use cooperative signaling via the TCR/CD3 complex and CD2 to activate and redirect resting cytotoxic T cells," *J. Immunol* 147:60, 1991.

U.S. National Library of Medicine, "Flavopiridol in Treating Patients With Previously Treated Chronic Lymphocytic Leukemia or Lymphocytic Lymphoma," Apr. 9, 2003, URL=https://www.clinicaltrials.gov/ct2/show/NCT00058240?term=alvocidib&rank=16, retrieved Dec. 11, 2018, 10 pages.

U.S. National Library of Medicine, "Flavopiridol in Treating Patients With Relapsed or Refractory Lymphoma or Multiple Myeloma," Jun. 3, 2005, URL=https://www.clinicaltrials.gov/ct2/show/study/NCT00112723?term=alvocidib&rank=8, retrieved Dec. 11, 2018, 14 pages.

U.S. National Library of Medicine, "Ph I Study of Alvocidib and Cytarabine/Daunorubicin (7+3) in Patients with Newly Diagnosed Acute Myeloid Leukemia (AML)", ClinicalTrials.gov, Identifier, NCT03298984, First Posted Oct. 2, 2017, Last Update Posted Mar. 14, 2019, retrieved from https://clinicaltrials.gov/ct2/show/study/NCT03298984, 8 pages.

Valencia et al., "A new reliable fluorescence in situ hybridization method for identifying multiple specific cytogenetic abnormalities in acute myeloid leukemia," *Leukemia & Lymphoma* 51(4):680-685, 2010.

Vaquero et al., "Extracellular matrix proteins protect pancreatic cancer cells from death via mitochondrial and nonmitochondrial pathways," *Gastroenterology* 125(4):1188-1202, 2003.

Vaux et al., "Bcl-2 gene promotes haemopoietic cell survival and cooperates with c-myc to immortalize pre-B cells," *Nature* 335(6189):440-442, 1988.

Venkat, "Flavopiridol: A Drug that May Save Lives," 2004, retrieved from https://web.archive.org/web/20060615112217/http://clltopics.org/Chemo/flavopiridol.htm, 7 pages.

Venugopal et al., "A Phase I Study of Quisinostat (JMJ-26481585), an Oral Hydroxamate Histone Deacetylase Inhibitor with Evidence of Target Modulation and Antitumor Activity, in Patients with Advanced Solid Tumors," *Clinical Cancer Research* 19:4262-4272, 2013.

Verhoeyen et al., "Reshaping Human Antibodies: Grafting an Antilysozyme Activity," *Science* 239:1534-1536, 1988.

Ververis et al., "Histone deacetylase inhibitors (HDACIs): multitargeted anticancer agents," *Biologics: Targets and Therapy* 7:47-60, 2013.

Villela et al., "Acute Myeloid Leukaemia: Optimal Management and Recent Developments," *Drugs* 71(12):1537-1550, 2011.

Vitetta et al., "Redesigning Nature's Poisons to Create Anti-Tumor Reagents," *Science* 238:1098-1104, 1987.

Vives et al., "A Truncated HIV-1 Tat Protein Basic Domain Rapidly Translocates through the Plasma Membrane and Accumulates in the Cell Nucleus," *J. Biol. Chem.* 272(25):16010-16017, 1997.

(56) References Cited

OTHER PUBLICATIONS

Vo et al., "Relative Mitochondrial Priming of Myeloblasts and Normal HSCs Determines Chemotherapeutic Success in AML," Cell 151:344-355, 2012.

Vo, "Mitochondrial Priming Determines Chemotherapeutic Response in Acute Myeloid Leukemia," Dissertation, Harvard University, 119 pages, Apr. 5, 2012.

Wang et al., "Bid: A Novel BH3 Domain-Only Death Agonist," Genes & Development 10(22):2859-2869, 1996.

Wang et al., "Cell Permeable Bcl-2 binding peptides: A Chemical Approach to Apoptosis Induction in Tumor Cells," Cancer Res. 60:1498-1502, 2000.

Wang et al., "Structure based discovery of an organic compound that binds Bcl-2 protein and induces apoptosis of tumor cells," PNAS 97:7124-7129, 2000.

Wang et al., "Synthesis of pochoxime prodrugs as potent HSP90 inhibitors," Bioorganic & Medicinal Chemistry Letters 19:3836-3840, 2009.

Wang, "The Expanding Role of Mitochondria in Apoptosis," Genes Dev 15:2922-2933, 2001.

Warner et al., "Predicting Response to Alvocidib by Mitochondrial Profiling," U.S. Appl. No. 15/134,051, filed Apr. 20, 2016, 87 pages.

Wei et al., "Proapoptotic BAX and BAK: A Requisite Gateway to Mitochondrial Dysfunction and Death," Science 292(5517):727-730, 2001.

Wei et al., "tBID, a membrane-targeted death ligand, oligomerizes BAK to release cytochrome c," Genes & Development 14:2060-2071, 2000.

Weinstein et al., "Addiction to Oncogenes—the Achilles Heal to Cancer," Science 297:63-64, 2002.

Weniger et al., "Treatment-Induced Oxidative Stress and Cellular Antioxidant Capacity Determine Response to Bortezomib in Mantle Cell Lymphoma," Clin. Cancer Res. 17(15):5101-5112, 2011.

Werner et al., "Bcl-2 Family Member Bfl-1/A1 Sequesters Truncated Bid to Inhibit its Collaboration With Pro-Apoptotic Bak or Bax," J. Biol. Chem 277(25):22781-22788, 2002.

Westerhoff et al., "Magainins and the disruption of membrane-linked free-energy transduction," Proc. Natl. Acad. Sci USA 86(17):6597-6601, 1989.

Whatcott et al., "Alvocidib Potentiates the Activity of Venetoclax in Preclinical Models of Acute Myeloid Leukemia," Blood 128(22):1652, 2016.

Wilkinson, "Immunochemical techniques inspire development of new antibody purification methods," The Scientist 14(8):25-28, 2000.

Willis et al., "Apoptosis Initiated When BH3 Ligands Engage Multiple Bcl-2 Homologs, not Bax or Bak," Science 315:856-859, 2007.

Willis et al., "Proapoptotic Bak is sequestered by Mcl-1 and Bcl-xL, but not Bcl-2, until displaced by BH3-only proteins," Genes Dev. 19:1294-1305, 2005.

Wolff et al., "Monoclonal antibody homodimers: Enhanced antitumor activity in Nude Mice," Cancer Research 53:2560-2565, 1993.

Wolter et al., "Movement of Bax from the Cytosol to Mitochondria during Apoptosis," J. Cell. Biol 139(5):1281-1292, 1997.

Worland et al., "Alteration of the Phosphorylation State of p34cdc2 Kinase by the Flavone L86-8275 in Breast Carcinoma Cells: Correlation with Decreased H1 Kinase Activity," Biochem. Pharmacol 46:1831-1840, 1993.

Woyach et al., "Targeted therapies in CLL: mechanisms of resistance and strategies for management," Blood 126:471-477, 2015.

Wyatt et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crysallography and Structure Based Drug Design," J. Med. Chem. 51:4986-4999, 2008.

Yamaguchi et al., "Bcl-XL Protects BimEL-induced Bax Conformational Change and Cytochrome c Release Independent of Interacting with Bax or BimEL," J. Biol. Chem 277(44):41604-41612, 2002.

Yamauchi, "Incorporation of novel agents into the treatment for acute myeloid leukemia," Rinsho Ketsueki 59(10):1988-1996, 2018. (English Abstract Only).

Yang et al., "Bad, a Heterodimeric Partner for Bcl-XL and Bcl-2, Displaces Bax Promotes Cell Death," Cell 80:285-291, 1995.

Yang et al., "Calculation of Protein Conformation from Circular Dichroism," Methods Enzymol 130:208-269, 1986.

Yang et al., "A novel liposomal formulation of flavopiridol," International Journal of Pharmaceutics 365:170-174, 2009.

Yang et al., "Bone marrow stroma-mediated resistance to FLT3 inhibitors in FLT3-ITD AML is mediated by persistent activation of extracellular regulated kinase," British Journal of Haematology 164:61-72, 2014.

Yasuda et al., "BNIP3α: A Human Homolog of Mitochondrial Proapoptotic protein BNIP3," Cancer Res. 59:533-537, 1999.

Yeh et al., "Up-regulation of CDK9 kinase activity and Mcl-1 stability contributes to the acquired resistance to cyclin-dependent kinase inhibitors in leukemia," Oncotarget 6(5):2667-2679, 2014.

Yi et al., "Inhibition of Bid-induced apoptosis by Bcl-2. tBid insertion, Bax translocation, and Bax/Bak oligomerization suppressed," J. Biol. Chem. 278(19):16992-16999, 2003.

Yu et al., "Catalytic Site Remodeling of the DOT1L Methyltransferase by Selective Inhibitors," Nat Commun 3:1288, 2012.

Zeidner et al., "Randomized multicenter phase II study of flavopiridol (alvocidib), cytarabine, and mitoxantrone (FLAM) versus cytarabine/daunorubicin (7+3) in newly diagnosed acute myeloid leukemia," Haematologica 100(9):1172-1179, 2015.

Zeng et al., "Targeting the leukemia microenvironment by CXCR4 inhibition overcomes resistance to kinase inhibitors and chemotherapy in AML," Blood 113:6215-6224, 2009.

Zha et al., "BH3 Domain of BAD is Required for Heterodimerization with Bcl-XL and Pro-apoptotic Activity," J. Biol. Chem. 272(39):24101-24104, 1997.

Zha et al., "Posttranslational N-Myristoylation of BID as a Molecular Switch for targeting Mitochondria and Apoptosis," Science 290(5497):1761-1765, 2000.

Zha et al., "Serine Phosphorylation of Death Agonist BAD in Response to Survival Factor Results in Binding to 14-3-3 Not BCL-XL," Cell 87:619-628, 1996.

Zhai et al., "Clinical pharmacology and pharmacogenetics of flavopiridol 1-h i.v. infusion in patients with refractory neoplasms," Anti-Cancer Drugs 14:125-135, 2003.

Zhang et al., "Bcl-2 family proteins are essential for platelet survival," Cell Death Differ. 14(5):943-951, 2007.

Zhao et al., "The Making of I-BET762, a BET Bromodomain Inhibitor Now in Clinical Development," Journal of Medicinal Chemistry 56:7498-7500, 2013.

Zhou et al., "Flavopiridol enhances ABT-199 sensitivity in unfavourable-risk multiple myeloma cells in vitro and in vivo," Br. J. Cancer 118(3):388-397, 2018.

Zhou et al., "Novel mutant-selective EGFR kinase inhibitors against EGFR T790M," Nature 462(7276):1070-1074, 2009.

Zhu et al., "Development of venetoclax for therapy of lymphoid malignancies," Drug Des. Devel. Ther. 11:685-694, 2017.

Zong et al., "BH3-only proteins that bind pro-survival Bcl-2 family members fail to induce apoptosis in the absence of Bax and Bak," Genes & Development 15:1481-1486, 2001.

Kantarjian, et a, "Decitabine Improves Patient Outcomes in Myelodysplastic Syndromes" Cancer vol. 106 No. 8 pp. 1794-1803 (year: 2006).

Karp, et al., "Timed Sequential Therapy of Acute Leukemia with Flavopiridol: In Vitro Model for a Phase I Clinical Trial" Clinical Cancer Research vol. 9 pp. 3076-3315 (Year: 2003).

Hourigan, et al., "Development of Therapeutic Agents for Older Patients with Acute Myelogenous Leukemia" Current Opinion in Investigational Drugs vol. 11 No. 6 pp. 669-677 (Year: 2010).

Kimura, et al, "Antiproliferative and Antitumor Effects of Azacitidine Against the Human Myelodysplastic Syndrome Cell Line SKM-1" Anticancer Research vol. 32 pp. 795-798 (Year: 2012).

Bogenberger el al., "BCL-2 family proteins as 6-Azacylidine-sensitizing targets and determinants of response in myeloid malignancies", Leukemia (2014) 28, 1657-1665.

(56) References Cited

OTHER PUBLICATIONS

Arguello, F., et al., "Flavopiridol induces apoptosis of normal lymphoid cells, causes immunosuppression, and has potent antitumor activity in vivo against human leukemia and lymphoma xenografts", Blood, 91:2482-2490 (1998).
Bible, K.C., et al., "Cytoxic Synergy Between Flavopiridol (NSC 649890, 186-8275) and Various Antineoplastic Agents: The Importance of Sequence of Adminstration", American Association for Cancer Research, Baltimore MD, US, 57:3375-3380 (1997).
Brooks, E. E.,et al., "CVT-313, a specific and potent inhibitor of CDK2 that prevents neointimal formation", J. Biol. Chem., 272:299207-29911 (1997).
Buccisano, et al., "Prognostic and Therapeutic Implications of Minimal Residual Disease Detection in Acute Myeloid Leukemia", Blood, 119(2):332-341 (2012).
Buijis, A., et al., "A novel CBFA2 single-nucleotide Mutation in Familial Platelet Disorder with Propensity to Develop Myeloid Malignancies", Blood, 89(9):2856-2868 (2001).
CAS Registry No. 146426-40-6—Flavopiridol (2010).
Chan, D., et al., "Belinostat and Panobinostat (HDACI): in vitro and invivo sStudies in Thyroid Cancer", J. Cancer Res.Clin. Oncol., 139:1507-1514 (2013).
Chang, M. W., et al., "Adenovirus-medlated over-expression of the cyclin/cyclin-dependent kinase inhibitor, p21 inhibits vascular smooth muscle cell proliferation and neointima formation in the rat carotid artery model of balloon angioplasty", J. Clin. Invest., 96:2260-2268 (1995).
Chen, D., "Downregulation of cyclin-dependent kinase 2 activity and cyclin A promoter activity in vascular smooth muscle cells by p27(KIP1), an inhibitor of neointima formation in the rat carotid artery", J. Clin. Invest., 99:2334-2341 (1997).
Cheronis, "Semimicro Experimental Organic Chemistry," deGratt, pp. 67-69 (1958).
Chou,T.-C. and Talalay, P., "Quantitative Analysis of Dose-Effect Relationships: The Combined Effects of Multiple Drugs or Enzyme Inhibitors", Advances in Enzyme Regulation, 22:27-55 (1985).
Clowes, A. W., et al., "Significance of quiescent smooth muscle migration in the injured rat carotid artery", Circ. Res., 56:139-145 (1995).
De Young, M. B, and Dichek, D. A., "Gene therapy for restenosis", Circ. Res., 82:306-313 (1998).
Drees, M., eta l., "Flavopiridol (L86-8275): Selective antitumor activity in vitro and activity in vivo for prostate carcinoma cells", Clin. Cancer Res., 3:273-279 (1997).
Fernandez, et al., "Anthracycline Dose Intesification in Acute Myeloid Leukemia", New England Journal of Medicine, 361(13):1249-1259 (2009).
Geng, Y. J., et al.,"Apoptosis of vascular smooth muscle cells induced by in vitro stimulation with interferon-gamma, tumor necrosis factor-alpha, and interleukin-1 beta", Arterioscier. Thromb. Biol, 16:19-27 (1996).
Ghyczy, M., et al., "Electrophilic Methyl Groups Present in the Diet Ameliorate Pathological States Induced by Reductive and Oxidative Stress: A Hypothesis", Britis Journal of Nutrition, 85(4):409-414 (2001).
Gores, et al., "Selectively Targeting Mcl-1 for the Treatment of Acute Myelogeneous Leukemia and Solid Tumors", Genes & Development, 26:305-311 (2012).
Hunter, T., "Braking the cycle", Cell, 75:839-841 (1993).
Hunter, T., "Protein kinases and phosphatases: The yin and yang of protein phosphorylation and signaling", Cell, 80:225-236 (1995).
Kearney, M., et al., "Histopathology of in-stent restenosis in patients with peripheral artery disease", Circulation, 95:1998-2002 (1997).
Lazarus, et al., "High-Dose Cytosine Arabinoside and Daunorubicin as Primary Therapy in Elderly Patients with Acute Myelogenous Leukemia", Cancer, 63:1055-1059 (1989).
Lemke, et al., "Immunobiology of the TAM Receptors," Nature Reviews Immunology, 8:327-336 (2008).
Lin, K.H., et al., "Targeting MCL-1/BCL-XL Forestalls the Acquisition of Resistance to ABT-1999 in Acutes Myeloid Leukemia", Scientific Reports, 6(1): 9 pp. 2016.
Mann, M. J., et al., "Cell cycle inhibition preserves endothelial function in genetically engineered rabbit vein grafts", J. Clin. Invest., 99:1295-1301 (1997).
Morishita, R., et al., "A gene therapy strategy using a transcription factor decoy of the E2F binding site inhibits smooth muscle proliferation in vivo", Proc. Natl. Acad. Sci. USA, 92:5855-5859 (1995).
Motwani, M., et al., "Sequential Dependent Enhancement of Caspase Activation and Apoptosis by Flavopiridol on Paclitaxel-Treated Human Gastric and Breast Cancer Cells", Clinical Cancer Research, The American Association for Cancer Research, 5(7):1876-1883 (1996).
Nagai, et al., Studies on Psychotropic Agents. VI. Synthesis of 1'-Methylspiro[6-fluoroindan-1, 3'-pyrrolidine]-3-one and Related Compounds, Chem and Pharm Bull, 28(5):1387-1393 (1980).
O'Brien, E. R., et al., "Proliferation in primary and restenotic coronary atherectomy tissue: implications for anti-proliferative therapy", Circ. Res., 73:223-231 (1993).
Otsuka, et al., "Effect of Polymorphic Forms of Bulk Powders on Pharmaceutical Properties of Carbamazepine Granules," Chem and Pharm Bull, 47(6):852-856 (1999).
Park, D. S., et al., "Inhibitors of cyclin-dependent kinases promote survival of post-mitotic neuronally differentiated PC12 cells and sympathetic neurons", J. Biol. Chem., 271:8161-8169 (1996).
Payne, D. M., et al., "Identification of the regulatory phosphorylation sites in pp42/mitogen-activated protein kinase (MAP kinase)", EMBO J., 10:885-892 (1991).
Ruef, J., "Flavopiridol Inhibits Smooth Muscle Cell Proliferation In Vitro and Neointimal Formation In Vivo After Carotid Injury in the Rat," Circulation, 100(6):659-665 (1999).
Ruef, J., "Induction of vascular endothelial growth factor in balloon-injured baboon arteries," Circulation Res, 81:24-33 (1997).
Ruef, J., "Induction of rat aortic smooth muscle cell growth by the lipid peroxidation product 4-hydroxy-2-nonenal," Circulation, 97:1071-1078 (1998).
Sata, M., et al., "Fas ligand gene transfer to the vessel wall inhibits neointima formation and overrides the adenovirus-mediated T cell response", Proc. Natl. Acad. Sci. USA, 95:1213-1217 (1998).
Schwartz, et al, "The intima: soil for atherosclerosis and restenosis", Circ. Res., 77:445-465 (1995).
Sirois, M.G., et al., "Antisense oligonucleotide inhibition of PDGFR-b receptor subunit expression directs suppression of intimal thickening", . Circulation,; 95:669-676 (1997).
Thomas, et al., "Phase I Clinical and Pharmacokinetic Trial Flavopiridol," Abstract #1496—Proceeding of the Annual Meeting of the American Association of Cancer Research, 38(14):222, Mar. 1997).
Wei, G. L., et al., "Temporally and spatially coordinated expression of cell cycle regulatory factors after angioplasty", Circ. Res., 80:418-426 (1997).
Belikov, V.G., in *Parameceutical Chemistry*, vol. 1, Moscow, High School, pp. 43-47 (1993) with English translation.
Kharkevich, D. A., In *Pharmacology* 3rd Ed., Moscow, Medicine, pp. 51-55, (1987) with English translation.
Adams et al., "The Bcl-2 Protein Family: Arbiters of Cell Survival," *Science* 281(5381):1322-1326, 1998.
Adlard et al., "Prediction of the response of colorectal cancer to systemic therapy," *The Lancet Oncology* 3:75-82, 2002.
Ait-Ikhlef et al., "The motoneuron degeneration in the wobbler mouse is independent of the overexpression of a Bcl2 transgene in neurons," *Neurosci Lett* 199:163-166, 1995.
Almarzooqi et al., "Comparison of Peripheral Blood versus Bone Marrow Blasts Immunophenotype in Pediatric Acute Leukemias," *Ibnosina Journal of Medicine and Biomedical Sciences*, pp. 195-204, 2011. (10 pages).
Altschul et al., *Nucleic Acids Res*. 25:3389-3402, 1997.
Bae et al., "Underphosphorylated BAD interacts with diverse antiapoptotic BCL-2 family proteins to regular apoptosis," *Apoptosis* 6:319-330, 2001.

(56) References Cited

OTHER PUBLICATIONS

Barretina et al., "The Cancer Cell Line Encyclopedia enables predictive modelling of anticancer drug sensitivity," *Nature* 483(7391):603-607, 2012; Erratum in: *Nature* 492(7428):290, 2012.
Bearss, "NOXA Priming—Predictive Biomarker for Patients With Acute Myeloid Leukemia to Improve Treatment Outcomes," 2016, retrieved from https://openforum.hbs.org/challenge/precision-medicine/submit-ideas/noxa-priming-predic . . . , 7 pages.
Bearss, "Targeting MCL1 dependent cancers by CDK9 inhibition," Abstract for Keynote Address, 9th International Conference on Leukemia and Hematologic Oncology, Oct. 5-6, 2017 London, UK, *J Hematol Thrombo Dis* 5(5 Suppl), 2017.
Blachly et al., "Emerging Drug Profile: Cyclin-Dependent Kinase Inhibitors," *Leuk Lymphoma* 54:2133-2143, 2013. (22 pages).
Bodet et al., "BH3-only protein Bik is involved in both apoptosis induction and sensitivity to oxidative stress in multiple myeloma," *Br. J. Cancer* 103:1808-1814, 2010.
Bogenberger et al., "Combined venetoclax and alvocidib in acute myeloid leukemia," *Oncotarget* 8(63):107206-107222, 2017.
Bose et al., "Mcl-1 as a therapeutic target in acute myelogenous leukemia (AML)," *Leukemia Research Reports* 2:12-14, 2013.
Bouillet et al., "Proapoptotic Bcl-2 Relative Bim Required for Certain Apoptotic Responses, Leukocyte Homeostasis, and to Preclude Autoimmunity," *Science* 286:1735-1738, 1999.
Boyd et al., "Bik, a novel death-inducing protein shares a distinct sequence motif with Bcl-2 family proteins and interacts with viral and cellular survival-promoting proteins," *Oncogene* 11(9):1921-1928, 1995.
Brady et al., "Reflections on a peptide," *Nature* 368:692-693, 1994.
Braun et al., "Preclinical Study of the Bromodomain Inhibitor OTX015 in Acute Myeloid (AML) and Lymphoid (ALL) Leukemias," *Blood* 122:4218, 2013. (5 pages) (Abstract Only).
Brennan et al., "Preparation of Bispecific Antibodies by Chemical Recombination of Monoclonal Immunoglobulin G1 Fragments," *Science* 229:81, 1985.
Brunelle et al., "MCL-1-dependent leukemia cells are more sensitive to chemotherapy than BCL-2-dependent counterparts," *J. Cell. Biol.* 187(3):429-442, 2009.
Brunetto et al., "First-in-human, Pharmacokinetic and Pharmacodynamic Phase I Study of Resminostat, and Oral Histone Deacetylase Inhibitor, in Patients with Advanced Solid Tumors," *Clinical Cancer Research* 19:5494-5504, 2013.
Buggy et al., "CRA-024781: a novel synthetic inhibitor of histone deacetylase enzymes with antitumor activity in vitro and in vivo," *Mol Cancer Ther* 5:1309-1317, 2006.
Buron et al., "Use of human cancer cell lines mitochondria to explore the mechanisms of BH3 peptides and ABT-737-induced mitochondrial membrane permeabilization," *PLoS One* 5(3):e9924, 2010.
Byrd et al., "Flavopiridol Induces Apoptosis in Chronic Lymphocytic Leukemia Cells via Activation of Caspase-3 Without Evidence of bcl-2 Modulation or Dependence on Functional p53," *Blood* 92:3804-3816, 1998.
Byrd et al., "Chronic Lymphocytic Leukemia," *Hematology*, pp. 163-183, 2004. (21 pages).
Byrd et al., "Flavopiridol Administered as a Pharmacologically-Derived Schedule Demonstrates Marked Clinical Activity in Refractory, Genetically High Risk, Chronic Lymphocytic Leukemia (CLL)," *Blood* 104:341, 2004. (2 pages).
Byrd et al., "Sequential Phase II Studies of Flavopiridol by 72-Hour Continuous Infusion and 1-Hour Intravenous Bolus for the Treatment of Relapsed B-Cell Chronic Lymphocytic Leukemia: Results from CALGB Study 19805," *Blood* 104:3485, 2004. (2 pages).
Byrd et al., "Treatment of Relapsed Chronic Lymphocytic Leukemia by 72-Hour Continuous Infusion or 1-Hour Bolus Infusion of Flavopiridol: Results from Cancer and Leukemia Group B Study 19805," *Clin Cancer Res* 11:4176-4181, 2005.
Byrd et al., "Flavopiridol administered using a pharmacologically derived schedule is associated with marked clinical efficacy in refractory, genetically high-risk chronic lymphocytic leukemia," *Blood* 109:399-404, 2007.
Calin et al., "A MicroRNA Signature Associated with Prognosis and Progression in Chronic Lymphocytic Leukemia," *N. Engl. J. Med.* 353:1793-1801, 2005.
Carlson et al., "Flavopiridol Induces $G_1$ Arrest with Inhibition of Cyclin-dependent Kinase (CDK)2 and CDK4 in Human Breast Carcinoma Cells," *Cancer Research* 56:2973-2978, 1996.
Caron et al., "Engineered Humanized Dimeric Forms of IgG Are More Effective Antibiotics," *J. Exp. Med.* 176:1191-1195, 1992.
Cartron et al., "The first α Helix of Bax Play a Necessary Role in its Ligand-Induced Activation by the BH3-Only Proteins Bid and PUMA," *Mol. Cell.* 16:807-818, 2004.
Certo et al., "Mitochondria Primed by Death Signals Determine Cellular Addiction to Antiapoptotic BCL-2 Family Members," *Cancer Cell* 9:351-365, 2006.
Chao et al., "Flavopiridol Inactivates P-TEFb and Blocks Most RNA Polymerase II Transcription in Vivo," *The Journal of Biological Chemistry* 276:31793-31799, 2001.
Chao et al., "Flavopiridol Inhibits P-TEFb and Blocks HIV-1 Replication," *The Journal of Biological Chemistry* 275:28345-28348, 2000.
Chen et al., "Caspase cleavage of BIMel triggers a positive feedback amplification of apoptotic signaling," *Proc. Natl. Acad. Sci. USA* 101(5):1235-1240, 2004.
Chen et al., "Differential Targeting of Prosurvival Bcl-2 Proteins by Their BH3-Only Ligands Allows Complementary Apoptotic Function," *Molecular Cell* 17:393-403, 2005.
Chen et al., "Transcription inhibition by flavopiridol: mechanism of chronic lymphocytic leukemia cell death," *Blood* 106:2513-2519, 2005.
Chen et al., "Mcl-1 Down-regulation Potentiates ABT-737 Lethality by Cooperatively Inducing Bak Activation and Bax Translocation," *Cancer Res* 67(2):782-791, 2007.
Chen et al., "Mechanism of action of SNS-032, a novel cyclin-dependent kinase inhibitor in chronic lymphocytic leukemia," *Blood* 113:4637-4645, 2009.
Cheng et al., "Bax-independent inhibition of apoptosis by Bcl-Xl," *Nature* 379:554-556, 1996.
Cheng et al., "BCL-2, BCL-Xl Sequester BH3 Domain-Only Molecules Preventing BAX- and BAK-Mediated Mitochondrial Apoptosis," *Mol. Cell* 8(3):705-711, 2001.
Cheson et al., "National Cancer Institute-Sponsored Working Group Guidelines for Chronic Lymphocytic Leukemia: Revised Guidelines for Diagnosis and Treatment," *Blood* 87:4990-4997, 1996.
Chipuk et al., "Direct Activation of Bax by p53 Mediates Mitochondrial Membrane Permeabilization and Apoptosis," *Science* 303:1010-1014, 2004.
Chittenden et al., "A conserved domain in Bak, distinct from BH1 and BH2, mediates cell death and protein binding functions," *EMBO J* 14(22):5589-5596, 1995.
Chittenden et al., "Induction of apoptosis by the Bcl-2 homologue Bak," *Nature* 374(6524):733-736, 1995.
Chonghaile et al., "Mimicking the BH3 domain to kill cancer cells," *Oncogene* 27:S149-S157, 2009.
Chonghaile et al., "Mitochondrial Apoptotic Priming Measured by BH3 Profiling Regulates Clinical Response to Chemotherapy in Myeloma and Acute Lymphoblastic Leukemia and Explains Therapeutic Index," Abstract 1442, 53rd ASH Annual Meeting and Exposition, Dec. 10-13, 2011, American Society of Hematology.
Chonghaile et al., "Pretreatment mitochondrial priming correlates with clinical responsive to cytotoxic chemotherapy," *Science* 334(6059):1129-1133, 2011. (6 pages).
Chonghaile et al., "Pretreatment mitochondrial priming correlates with clinical responsive to cytotoxic chemotherapy," *Science* 334(6059):1129-1133, 2011. Supporting Online Material, 36 pages.
Choudhary et al., "MCL-1 and BCL-xL-dependent resistance to the BCL-2 inhibitor ABT-199 can be overcome by preventing PI3K/AKT/mTOR activation in lymphoid malignancies," *Cell Death and Disease* 6:e1593, 2015. (12 pages).

(56) References Cited

OTHER PUBLICATIONS

Cole et al., "The EBV-Hybridoma technique and its application to human lung cancer," *Monoclonal Antibodies and Cancer Therapy*:77-96, 1985.
Conaway et al., "The Mediator Complex and Transcription Elongation," *Biochim Biophys Acta* 1829:69-75, 2013. (16 pages).
Cory et al., "The Bcl2 Family: Regulators of the Cellular Life-or-Death Switch," *Nat. Rev. Cancer* 2(9):647-656, 2002.
Cosulich et al., "Regulation of apoptosis by BH3 domains in a cell-free system," *Curr. Biol* 7(12):913-920, 1997.
Cote et al., "Generation of human monoclonal antibiotics reactive with cellular antigens," *Proc. Natl. Acad. Sci. USA* 80:2026-2030, 1983.
Czabotar et al., "Bax Activation by Bim?," *Cell Death and Differentiation* 16:1187-1191, 2009.
Czabotar et al., "Structural insights into the degradation of Mcl-1 induced by BH3 domains," *PNAS* 104:6217-6222, 2007.
Czech et al., "Antitumoral activity of flavone L 86-8275," *International Journal of Oncology* 6:31-36, 1995.
Daigle et al., "Potent Inhibition of DOT1L as Treatment of MLL-fusion Leukemia," *Blood* 122:1017-1025, 2013.
Danial et al., "Cell Death: Critical Control Points," *Cell* 116:205-219, 2004.
Davids et al., "BH3 profiling demonstrates that restoration of apoptotic priming contributes to increased sensitivity to PI3K inhibition in stroma-exposed chronic lymphocytic leukemia cells," *Blood* 118(21): Nov. 18, 2011, Abstract.
Davids et al., "Targeting the B-cell lymphoma/leukemia 2 family in cancer," *J Clin Oncol* 30(25):3127-3135, 2012.
Dawson, M.A., et al., "Inhibition of BET Recruitment to Chromatin as an Effective Treatment for MLL-Fusion Leukaemia", Nature, 478:328-333 (2011).
De Azevedo Jr. et al., "Structural basis for inhibition of cyclin-dependent kinase 9 by flavopiridol," *Biochemical and Biophysical Research Communications* 293:566-571, 2002.
Debrincat et al., "BCL-2 is dispensable for thrombopoiesis and platelet survival," *Cell Death & Disease* 6:e1721, 2015. (8 pages).
DeGrado, "Designs of peptides and proteins," *Adv. Protein Chem* 39:51-124, 1988.
Deng et al., "BH3 Profiling Identifies Three Distinct Classes of Apoptotic Blocks to Predict Response to ABT-737 and Conventional Chemotherapeutic Agents," *Cancer Cell* 12:171-185, 2007.
Derenne et al., "Antisense strategy shows that Mcl-1 rather than Bcl-2 of Bcl-xl is an essential survival protein of human myeloma cells," *Blood* 100:194-199, 2002.
Desagher et al., "Bid-induced Conformational Change of Bax Is Responsible for Mitochondrial Cytochrome c Release during Apoptosis," *J. Cell Biol* 144(5):891-901, 1999.
Dettman et al., "Abstract 3400: Mitochondrial profiling in AML patients treated with an Alvocidib containing regimen reveals MCL1 dependency in responder bone marrow," *Cancer Res* 75:3400, 2015. (2 pages).
Di Lisa et al., "Mitochondrial Function and Cell Injury in Single Cardiac Myocytes Exposed to Anoxia and Reoxygenation," *Transplant. Proc.* 27(5):2829-2830, 1995.
Di Lisa et al., "Mitochondrial membrane potential in single living adult rat cardiac myocytes exposed to anoxia or metabolic inhibition," *J. Physiol* 486(1):1-13, 1995.
Diamandis et al., *Immunoassays*, Academic Press, Inc., NY, 1996.
Dinnen et al., "Redirecting Apoptosis to Aponecrosis Induces Selective Cytotoxicity to Pancreatic Cancer Cells through Increased ROS, Decline in ATP Levels, and VDAC," *Molecular Cancer Therapeutics* 12:2792-2803, 2013.
Döhner et al., "Genomic Aberrations and Survival in Chronic Lymphocytic Leukemia," *N. Engl. J. Med.* 343:1910-1916, 2000.
Egle et al., "Bim is a suppressor of Myc-induced mouse B cell leukemia," *Proc. Natl. Acad. Sci USA* 101(16):6164-6169, 2004.
Ellerby et al., "Anti-cancer activity of targeted pro-apoptotic peptides," *Nat. Med.* 5(9):1032-1038, 1999.
Elliott et al., "Intracellular Trafficking and Protein Delivery by a Herpesvirus Structural Protein," *Cell* 88:223-233, 1997.
Elston et al., "Pathological prognostic factors in breast cancer. I. The value of histological grade in breast cancer: experience from a large study with long-term follow-up," *Histopathology* 19:403-410, 1991.
Ember et al., "Acetyl-lysine Binding Site of Bromodomain-Containing Protein 4 (BRD4) Interacts with Diverse Kinase Inhibitors," *ACS Chemical Biology* 9:1160-1171, 2014.
Eskes et al., "Bid Induces the Oligomerization and Insertion of Bax into the Outer Mitochondrial Membrane," *Mol. Cell. Biol.* 20(3):929-935, 2000.
Falkenberg et al., "Histone deacetylases and their inhibitors in cancer, neurological diseases and immune disorders," *Nature Reviews Drug Discovery* 13:673-691, 2014.
Fanidi et al., "Cooperative interaction between c-myc and -2 proto-oncogenes," *Nature* 359:554-556, 1992.
Filippakopoulos et al., "Selective inhibition of BET bromodomains," *Nature* 468:1067-1073, 2010.
Filippakopoulos et al., "Targeting bromodomains: epigenetic readers of lysine acetylation," *Nature Reviews Drug Discovery* 13:337-356, 2014.
Fish et al., "Identification of a Chemical Probe for Bromo and Extra C-Terminal Bromodomain Inhibition through Optimization of a Fragment-Derived Hit," *Journal of Medicinal Chemistry* 55:9831-9837, 2012.
Fiskum et al., "[21] Apoptosis-Related Activities Measured with Isolated Mitochondria and Digitonin-Permeabilized Cells," *Methods in Enzymology* 322:222-234, 2000.
Fiskus et al., "Highly Active Combination of BRD4 Antagonist and Histone Deacetylase Inhibitor against Human Acute Myelogenous Leukemia Cells," *Molecular Cancer Therapeutics* 13:1142-1154, 2014.
Flinn et al., "Flavopiridol Administered as a 24-Hour Continuous Infusion in Chronic Lymphocytic Leukemia lacks Clinical Activity," *Leukemia Res* 29:1253-1257, 2005.
Foight et al., "Designed BH3 Peptides with High Affinity and Specificity for Targeting Mcl-1 in Cells," *ACS Chem. Biol.* 9:1962-1968, 2014.
Frankel et al., "Activity of synthetic peptides from the Tat protein of human immunodeficiency virus type 1," *Proc. Natl. Acad. Sci. USA* 86:7397-7401, 1989.
Freidman et al., "Precision medicine for cancer with next-generation functional diagnostics," *Nat Rev Cancer* 15(12):747-756, 2015.
Fuchs et al., "Pathway for Polyarginine Entry into Mammalian Cells," *Biochemistry* 43(9):2438-2444, 2004.
Fukui et al., "The Analysis of the Effect of JQ1 and Flavopiridol on Chondrocytes under Inflammatory Stimuli," ORS 2014 Annual Meeting, 4 pages.
Futaki et al., "Arginine-rich Peptides: An Abundant Source of Membrane-Permeable Peptides Having Potential as Carriers for Intracellular Protein Delivery," *J. Biol. Chem* 276(8):5836-5840, 2001.
Gerber et al., "Association of acute myeloid leukemia's most immature phenotype with risk groups and outcomes," *Haematologica* 101(5): 607-616, 2016.
Geserick et al., "The ratio of Mcl-1 and Noxa determines ABT737 resistance in squamous cell carcinoma of the skin," *Cell Death and Disease* 5:e1412, 2014. (14 pages).
Giles et al., "A Phase I Study of Intravenous LBH589, a Novel Cinnamic Hydroxamic Acid Analogue Histone Deacetylase Inhibitor in Patients with Refractory Hematologic Malignancies," *Clin Cancer Res* 12:4628-4635, 2006.
Gojo et al., "The Cyclin-dependent Kinase Inhibitor Flavopiridol Induces Apoptosis in Multiple Myeloma Cells through Transcriptional Repression and Down-Regulation of Mcl-1," *Clinical Cancer Research* 8:3527-3538, 2002.
Goldsmith et al., "BH3 peptidomimetics potentially activate apoptosis and demonstrate single agent efficacy in neuroblastoma," *Oncogene* 25:4525-4533, 2006.
Göttlicher et al., "Valproic acid defines a novel class of HDAC inhibitors inducing differentiation of transformed cells," *The EMBO Journal* 20:6969-6978, 2001.

(56) References Cited

OTHER PUBLICATIONS

Green et al., "A matter of life and death," *Cancer Cell* 1:19-30, 2002.
Green et al., "The Pathophysiology of Mitochondrial Cell Death," *Science* 305:626-629, 2004.
Green, "Life, Death, BH3 Profiles, and the Salmon Mousse," *Cancer Cell* 12:97-99, 2007.
Griffiths et al., "Cell Damage-induced Conformational Changes of the Pro-Apoptotic Protein Back In Vivo Precede the Onset of Apoptosis," *J. Cell. Biol.* 144(5):903-914, 1999.
Gross et al., "Enforced dimerization of BAX results in its translocation, mitochondrial dysfunction and apoptosis," *EMBO J* 17(14):3878-3885, 1998.
Gruber et al., "Efficient Tumor Cell Lysis Mediated by a Bispecific Single Chain Antibody Expressed in *Escherichia coli*," *J. Immunol* 152:5368-5374, 1994.
Guha, "Cyclin-dependent kinase inhibitors move into Phase III," *Nature Reviews Drug Discovery* 11:892-894, 2012.
Gul et al., "Apoptotic blocks and chemotherapy resistance: strategies to identify Bcl-2 protein signatures," *Briefings in Functional Genomics and Proteomics* 7(1):27-34, 2008.
Hanahan et al., "Heritable formation of pancreatic β-cell tumors in transgenic mice expressing recombinant insulin/simian virus 40 oncogenes," *Nature* 315:115-122, 1985.
Hanahan et al., "The Hallmarks of Cancer," *Cell* 100:57-70, 2000.
Hans et al., "β-Carbolines induce apoptosis in cultured cerebellar granule neurons via the mitochondrial pathway," *Neuropharmacology* 48:105-117, 2005.
Harada et al., "Survival factor-induced extracellular signal-regulated kinase phosphorylates BIM, inhibiting its association with BAX and proapoptotic activity," *Proc. Natl. Acad. Sci. USA* 101(43):15313-15317, 2004.
Harada et al., "Discovery of potent and orally bioavailable 17β-hydroxysteroid dehydrogenase type 3 inhibitors," *Bioorganic & Medicinal Chemistry* 20:3242-3254, 2012.
Haws et al., "E881: By an MCL-1-Dependent Mechanism, Alvocidib Potentiates the Activity of Cytarabine and Mitoxantrone When Administered in a Time Sequential Regimen in AML," Hematologica 102(Suppl. 2):362, 2017. (1 page).
Haws et al., "E1204: Alvocidib Synergizes With Venetoclax in Preclinical Models of Multiple Myeloma," *Hematologica* 102(Suppl. 2):495, 2017. (1 page).
Hemann et al., "Evasion of the p53 tumour surveillance network by tumour-derived MYC mutants," *Nature* 436:807-811, 2005.
Hemann et al., "Suppression of tumorigenesis by the p53 target PUMA," *Proc. Natl. Acad. Sci. USA* 101(25):9333-9338, 2004.
Hengartner et al., "*C. elegans* Cell Survival ced-9 Encodes a functional Homolog of the Mammalian Proto-Oncogene bcl-2," *Cell* 76:665-676, 1994.
Hirst et al., "Application of Non-Parametric Regression to Quantitative Structure-Activity Relationships," *Bioorganic & Medicinal Chemistry* 10:1037-1041, 2002.
Hnisz et al., "Super-Enhancers in the Control of Cell Identity and Disease," *Cell* 155:934-947, 2013.
Holinger et al., "Bak BH3 Peptides Antagonize Bcl-xl Function and Induce Apoptosis through Cytochrome c-independent Activation of Caspases," *J. Biol. Chem.* 274(19):13298-13304, 1999.
Holliger et al., "Diabodies: Small bivalent and bispecific antibody fragments," *Proc. Natl. Acad. Sci. USA* 90:6444-6448, 1993.
Hoogenboom et al., "By-passing Immunisation, Human Antibodies from Synthetic Repertoires of Germlike VH Gene Segments rearranged in Vitro," *J. Mol. Biol.* 227:381-388, 1992.
Hopp et al., "Prediction of protein antigenic determinants from amino acid sequences," *Proc. Natl. Acad. Sci. USA* 78:3824-3828, 1981.
Hoppel et al., "The action of digitonin on rat liver mitochondria. The effects on enzyme content," *Biochem J.* 107(3):367-375, 1968.
Hsu et al., "Nonionic Detergents Induce Dimerization among Members of the Bcl-2 Family," *J. Biol. Chem* 272(21):13829-13834, 1997.
Huang et al., "BH3-Only Proteins—Essential Initiators of Apoptotic Cell Death," *Cell* 103:839-842, 2000.
Huber et al., "Profile of venetoclax and its potential in the context of treatment of relapsed or refractory chronic lymphocytic leukemia," *Onco. Targets Ther.* 10:645-656, 2017.
Huse et al., "Generation of a large Combinatorial Library of the Immunoglobulin Repertoire in Phage Lambda," *Science* 246:1275-1281, 1989.
Innocenti et al., "Flavopiridol Metabolism in Cancer Patients Is Associated with the Occurrence of Diarrhea," *Clinical Cancer Research* 6:3400-3405, 2000.
Inohara et al., "Harakiri, a novel regulator of cell death, encodes a protein that activates apoptosis and interacts selectively with survival-promoting proteins Bcl-2 and Bcl-Xl," *EMBO J* 16(7):1686-1694, 1997.
Ishizawa et al., "Mitochondrial Profiling of Acute Myeloid Leukemia in the Assessment of Response to Apoptosis Modulating Drugs," *PLoS One* 10:e0138377, 2015.
Jackson et al., "Heat shock induces the release of fibroblast growth factor 1 from NIH 3T3 cells," *Proc. Natl. Acad. Sci. USA* 89:10691-10695, 1992.
Jameson et al., "A rationally designed CD4 analogue inhibits experimental allergic encephalomyelitis," *Nature* 368:744-746, 1994.
Jones et al., "Replacing the complementarily-determining regions in a human antibody with those from a mouse," *Nature* 321:522-525, 1986.
Jonkers et al., "Oncogene addiction: Sometimes a temporary slavery," *Cancer Cell* 6:535-538, 2004.
Karp et al., "Phase I and pharmacokinetic study of flavopiridol followed by 1-beta-D-arabinofuranosylcytosine and mitoxantrone in relapsed and refractory adult acute leukemias," Clin. Cancer Res. 11(23):8403-8412, 2005.
Karp et al., "Sequential flavopiridol, cytosine arabinoside, and mitoxantrone: a phase II trial in adults with poor-risk acute myelogenous leukemia," *Clin. Cancer Res.* 13(15 Pt. 1):4467-4473, 2007.
Kasper et al., "Targeting MCL-1 sensitizes FLT3-ITD-positive leukemias to cytotoxic therapies," *Blood Cancer J* 2: 10 pages, 2012.
Keating et al., "Results of First Salvage Therapy for Patients Refractory to a Fludarabine Regimen in Chronic Lymphocytic Leukemia," *Leuk. Lymph.* 43:1755-1762, 2002.
Keating et al., "Therapeutic role of alemtuzumab (Campath-1H) in patients who have failed fludarabine: results of a large international study," *Blood* 99:3554-3561, 2002.
Kelekar et al., "Bad is a BH3 Domain-Containing Protein that Forms an Inactivating Dimer with Bcl-xl," *Mol. Cell. Biol.* 17(12):7040-7046, 1997.
Kelekar et al., "Bcl-2-family proteins: the role of the BH3 domain in apoptosis," *Trends in Cell Biol* 8:324-330, 1998.
KG-1a, ATCC® CCC-246.1™ ATCC Product Sheet, 3 pages, May 31, 2013.
Kim et al., "Abstract 3728: Targeting MCL-1 expression, through the inhibition of CDK9 and super enhancer driven transcription, offers multiple opportunities for rational drug combinations," *Cancer Research* 76(14 Suppl.):3728, 2016.
Kim et al., "Alvocidib Synergizes with Cytarabine and Daunorubicin (7+3) in Preclinical Models of Acute Myeloid Leukemia", *EHA Learning Center*, May 18, 2017, retrieved from https://learningcenter.ehaweb.org/eha/2017/22nd/180678.
Kitada et al., "Protein kinase inhibitors flavopiridol and 7-hydroxy-staurosporine down-regulate antiapoptosis proteins in B-cell chronic lymphocytic leukemia," *Blood* 96:393-397, 2000.
Kohler et al., "Continuous cultures of fused cells secreting antibody of predefined specificity," *Nature* 256:495-497, 1975.
König et al., "The Novel Cyclin-Dependent Kinase Inhibitor Flavopiridol Downregulates Bcl-2 and Induces Growth Arrest and Apoptosis in Chronic B-Cell Leukemia Lines," *Blood* 90:4307-4312, 1997.
Korsmeyer et al., "Pro-apoptotic cascade activates BID, which oligomeizes BAK or BAX into pores that result in the release of cytochrome c," *Cell Death Differ* 7(12):1166-1173, 2000.
Kozbor et al., "The production of monoclonal antibodies from human lymphocytes," *Immunol Today* 4:72-79, 1983.

(56) References Cited

OTHER PUBLICATIONS

Kryštof et al., "Cyclin-Dependent Kinase Inhibitors as Anticancer Drugs," *Current Drug Targets* 11:291-302, 2010.
Kuwana et al., "BH3 Domains of BH3-Only Proteins Differentially Regulate Bax-Mediated Mitochondrial Membrane Permeabilization Both Directly and Indirectly," *Mol. Cell.* 17:525-535, 2005.
Kuwana et al., "Bid, Bax, and Lipids Cooperate to Form Supramolecular Openings in the Outer Mitochondrial Membrane," *Cell* 111:331-342, 2002.
Kyte et al., "A Simple Method for displaying the Hydropathic Character of a protein," *J. Mol. Biol.* 157:105-132, 1982.
La Vieira et al., "Cell permeable BH3-peptides overcome the cytoprotective effect of Bcl-2 and Bcl-$X_L$," *Oncogene* 21:1963-1977, 2002.
Labi et al., "Targeting the Bcl-2-regulated apoptosis pathway by BH3 mimetics: a breakthrough in anticancer therapy?," *Cell Death and Differentiation* 15:977-987, 2008.
Leo et al., "Characterization of the Antiapoptotic Bcl-2 Family Member Myeloid Cell Leukemia-1 (Mcl-1) and the Stimulation of Its Message by Gonadotropins in the Rat Ovary," *Endocrinol* 140:5469-5477, 1999.
Letai et al., "Distinct BH3 domains either sensitize or activate mitochondrial apoptosis, serving as prototype cancer therapeutics," *Cancer Cell* 2:183-192, 2002.
Letai, "BH3 domains as BCL-2 inhibitors: prototype cancer therapeutics," *Expert Opin. Biol. Ther.* 3:293-304, 2003.
Letai et al., "Antiapoptotic BcL-2 is required for maintenance of a model leukemia," *Cancer Cell* 6:241-249, 2004.
Letai, "The BCL-2 network: Mechanistic insights and therapeutic potential," *Drug Disc. Today: Disease Mechanisms* 2(2):145-151, 2005.
Letai, "Perturbing cancer cell mitochondria to learn how to kill cancer with BH3 profiling," Broad Institute, Seminar Series on Cell Circuits and Epigenomics, Jul. 28, 2014, Presentation.
Li et al., "tsg 101: A Novel tumor susceptibility gene isolated by controlled Homozygous functional knockout of Allelic Loci in Mammalian Cells," *Cell* 85:319-329, 1996.
Li et al., "Cleavage of BID by Caspase 8 Mediates the Mitochondrial Damage in the Fas Pathway of Apoptosis," *Cell* 94(4):491-501, 1998.
Li et al., "Endonuclease G is an apoptotic Dnase when released from mitochondria," *Nature* 412:95-99, 2001.
Lin et al., "Seventy-Two Hour Continuous Infusion Flavopiridol in Relapsed and Refractory Mantle Cell Lymphoma," *Leukemia & Lymphoma* 43:793-797, 2002.
Lin et al., "Flavopiridol given as a 30-min intravenous (IV) bolus followed by 4-hr continuous IV infusion (CIVI) results in clinical activity and tumor lysis in refractory chronic lymphocytic leukemia (CLL)," *Journal of Clinical Oncology, 2004 ASCO Annual Meeting Proceedings (Post-Meeting Edition)* 22(14S):8564, 2004. (1 page).
Liu et al., "Bax conformational change is a crucial step for PUMA-mediated apoptosis in human leukemia," *BioChem. Biophys. Res. Commun.* 310(3):956-962, 2003.
Liu et al., "BH3-based Fusion Artificial Peptide Induces Apoptosis and Targets Human Colon Cancer," *Molecular Therapy* 17:1509-1516, 2009.
Liu et al., "CDKI-71, a novel CDK9 inhibitor, is preferentially cytotoxic to cancer cells compared to flavopiridol," *Int. J. Cancer* 130:1216-1226, 2012.
Lonberg et al., "Antigen-specific human antibodies from mice comprising four distinct genetic modifications," *Nature* 368:856-859, 1994.
Long et al., "Optimization and validation of mitochondria-based functional assay as a useful tool to identify BH3-like molecules selectively targeting anti-apoptotic Bcl-2 proteins," *BMC Biotechnol* 13:45, 2013.
Lovén et al., "Selective Inhibition of Tumor Oncogenes by Disruption of Super-Enhancers," *Cell* 153:320-334, 2013. (27 pages).

Lozanski et al., "Alemtuzumab is an effective therapy for chronic lymphocytic leukemia with p53 mutations and deletions," *Blood* 103:3278-3281, 2004.
Lu, H., et al., "Compensatory Induction of MYC Expression by Sustained CDK9 Inhibition via a BRD4-dependent Mechanism", eLife, 26 pages Jun. 17, 2015.
Luo et al., "Bid, a Bcl2 interacting protein, mediates cytochrome c release from mitochondria in response to activation of cell surface dell receptors," *Cell* 94(4):481-490, 1998.
Lutter et al., "The pro-apoptotic Bcl-2 family member tBid localizes to mitochondrial contact sites," *BMC Cell Biology* 2:22, 2001.
Marani et al., "Identification of Novel Isoforms of the BH3 Domain Protein Bim which Directly Activate Bax to Trigger Apoptosis," *Mol. Cell. Biol.* 22(11):3577-3589, 2002.
Marks et al., "By-passing Immunization human Antibodies from v-gene libraries displayed on phage," *J. Mol. Biol.* 222:581, 1991.
Marks et al., "By-passing Immunization: building high affinity human antibodies by chin shuffling," *Bio/Technology* 10:779-783, 1992.
Martin, "Opening the Cellular Poison Cabinet," *Science* 330:1330-1331, 2010.
Mason et al., "The Hypogondal mouse: reproductive functions restored by gene therapy," *Science* 234:1372-1378, 1986.
Matsushita et al., "A high-efficiency protein transduction system demonstrating the role of PKA in long-lasting long-term potentiation," *J. Neuroscience* 21:6000-6007, 2001.
Matsuzaki, "Why and how are peptide-lipid interactions utilized for self-defense?" *Biochem. Soc. Transactions* 29:598-601, 2001.
McDonnell et al., "bcl-2-Immunoglobulin Transgenic Mice Demonstrate Extended B Cell Survival and Follicular Lymphoproliferation," *Cell* 57:79-88, 1989.
Means et al., "Modifications to change properties," in *Chemical Modification of Protein*, Chapter 3, pp. 35-54, Holden-Day (1974).
Miller et al., "Therapeutic Strategies to Enhance the Anticancer Efficacy of Histone Deacetylase Inhibitors," *J. Biomed. Biotechnol.* 2011:17 pages, 2011.
Milstein et al., "Hybrid hybridomas and their use in immunohistochemistry," *Nature* 305:537-539, 1983.
Molassiotis et al., "Use of complementary and alternative medicine in cancer patients: A European survey," *Annals of Oncology* 16:655-663, 2005.
Montero et al., "Drug-induced death signaling strategy rapidly predicts cancer response to chemotherapy," *Cell* 160(5):977-990, 2015.
Moore et al., "Chronic lymphocytic leukemia requires BCL2 to sequester prodeath BIM, explaining sensitivity to BCL2 antagonist ABT-737," *J. Clin. Invest.* 117(1):112-121, 2007.
Moore et al., "BH3 profiling—measuring integrated function of the mitochondrial apoptotic pathway to predict cell fate decisions," *Cancer Lett* 332:202-205, 2013. (10 pages).
Morrison et al., "Success in specification," *Nature* 368:812-813, 1994.
Muchmore et al., "X-ray and NMR structure of human Bcl-xl, an inhibitor of programmed cell death," *Nature* 381:335-341, 1996.
Munson et al., "Ligand: A Versatile Computerized Approach for Characterization of Ligand-Binding Systems," *Analytical Biochemistry* 107:220-239, 1980.
Murthi et al., "Structure-Activity Relationship Studies of Flavopiridol Analogues," *Bioorganic & Medicinal Chemistry Letters* 10:1037-1041, 2000.
Naik et al., "An Antiinflammatory Cum Immunomodulatory Piperidinylbenzopyranone From *Dysoxylum binectariferum*: Isolation, Structure and Total Synthesis," *Tetrahedron* 44:2081-2086, 1988.
Nakano et al., "PUMA, a Novel Proapoptotic Gene, Is Induced by p53," *Molecular Cell* 7:683-694, 2001.
Narita et al., "bax interacts with the permeability transition pore to induce permeability transition and cytochrome c release in isolated mitochondria," *Proc. Natl. Acad Sci. USA* 95:14681-14686, 1998.
Neuberger et al., "Generating high-avidity human Mabs in mice," *Nature Biotechnology* 14:826, 1996.

(56) References Cited

OTHER PUBLICATIONS

Nguyen et al., "Azacitidine and decitabine have different mechanisms of action in non-small cell lung cancer cell lines," *Lung Cancer: Targets and Therapy* 1:119-140, 2010.
Noel et al., "Abstract C244: Development of the BET bromodomain inhibitor OTX015," *Molecular Cancer Therapeutics* 12(11): Supplement, 2013.
O'Brien et al., "Phase I and II Multicenter Study of Oblimersen Sodium, a Bcl-2 Antisense Oligonucleotide, in Patients With Advanced Chronic Lymphocytic Leukemia," *J. Clin. Oncol.* 23(30):7697-7702, 2005.
O'Connor et al., "Bim: a novel member of the Bcl-2 family that promotes apoptosis," *EMBO J* 17(2):384-395, 1998.
Oda et al., "Noxa, a BH3-Only Member of the Bcl-2 Family and Candidate Mediator of p53-Induced Apoptosis," *Science* 288:1053-1058, 2000.
Odore et al., "A phase I pharmacokinetic study of OTX015 for the treatment of patients with hematologic malignancies," *Cancer Research* 74(Supplement 19):LB-231, 2014. (4 pages) (Abstract Only).
Oh et al., "Conformational Changes in BID, a Pro-apoptotic BCL-2 Family Member, upon Membrane Binding," *J. Biol. Chem.* 280(1):753-767, 2005.
Okamoto et al., "Increased antitumor potential of the raloxifene prodrug, raloxifene diphosphate," *Int. J. Cancer* 122:2142-2147, 2008.
Oltersdorf et al., "An inhibitor of Bcl-2 family proteins induces regression of solid tumours," *Nature* 435:677-681, 2005.
Opferman et al., "Development and maintenance of B and T lymphocytes requires antiapoptotic MCL-1," *Nature* 426:671-676, 2003.
Oppermann et al., "High-content screening identifies kinase inhibitors that overcome venetoclax resistance in activated CLL cells," *Blood* 128(7):934-947, 2016.
Oscier et al., "Multivariate analysis of prognostic factors in CLL: clinical stage, IGVH gene mutational status, and loss or mutation of the p53 gene are independent prognostic factors," *Blood* 100:1177-1184, 2002.
Paoluzzi et al., "The BH3-only mimetic ABT-737 synergizes the antineoplastic activity of proteasome inhibitors in lymphoid malignancies," *Blood* 112:2906-2916, 2008.
Paquin et al., "Design and synthesis of 4-[(s-triazin-2-ylamino)methyl]-N-(2-aminophenyl)-benzamides and their analogues as a novel class of histone deacetylase inhibitors," *Bioorganic & Medicinal Chemistry Letters* 18:1067-1071, 2008.
Parker et al., "Early Induction of Apoptosis in Hematopoietic Cell Lines After Exposure to Flavopiridol," *Blood* 91:458-465, 1998.
Parry et al., "Dinaciclib (SCH 727965), a Novel and Potent Cyclin-Dependent Kinase Inhibitor," *Molecular Cell Therapy* 9:2344-2353, 2010.
Paruch et al., "Discovery of Dinaciclib (SCH 727965): A Potent and Selective Inhibitor of Cyclin-Dependent Kinases," *ACS Medicinal Chemistry Letters* 1:204-208, 2010.
Pepper et al., "Flavopiridol circumvents Bcl-2 family mediated inhibition of apoptosis and drug resistance in B-cell chronic lymphocytic leukaemia," *Br. J. Haematol* 114(1):70-77, 2001.
Perkins et al., "Frequency and Type of Serious Infections in Fludarabine-Refractory B-Cell Chronic Lymphocytic Leukemia and Small Lymphocytic Lymphoma," *Cancer* 94:2033-2039, 2002.
Phillips et al., "Loss in MCL-1 function sensitizes non-Hodgkin's lymphoma cell lines to the BCL-2-selective inhibitor venetoclax (ABT-199)," *Blood Cancer J.* 5:e368, 2015. (8 pages).
Picaud et al., "PFI-1, a Highly Selective Protein Interaction Inhibitor, Targeting BET Bromodomains," *Cancer Research* 73:3336-33346, 2013.
Piekarz et al., "Inhibitor of histone deacetylation, depsipeptide (FR901228), in the treatment of peripheral and cutaneous T-cell lymphoma: a case report," *Blood* 98:2865-2868, 2001.
Pierceall et al., "BH3 Profiling Discriminates Response to Cytarabine-Based Treatment of Acute Myelogenous Leukemia," *Mol. Cancer. Ther.* 12(12):2940-2949, 2013.
Pierceall et al., "Mcl-1 Dependence Predicts Response to Vorinostat and Gemtuzumab Ozogamicin in Acute Myeloid Leukemia," *Leuk Res* 38:564-568, 2014. (13 pages).
Pierceall et al., "Mitochondrial Priming of Chronic Lymphocytic Leukemia Patients Associates Bcl-$x_L$ Dependence with Alvocidib Response," *Leukemia* 28:2251-2254, 2014. (7 pages).
Pinkert et al., "An albumin enhancer located 10 kb upstream functions along with its promoter to direct efficient, liver-specific expression in transgenic mice," *Genes and Dev* 1:268-276, 1987.
Plumb et al., "Pharmacodynamic Response and Inhibition of Growth of Human Tumor Xenografts by the Novel Histone Deacetylase Inhibitor PXD101," *Molecular Cancer Therapeutics* 2:721-728, 2003.
Pode-Shakked et al., "Development tumourigenesis: NCAM as a purative marker for the malignant renal stem/progenitor cell population," *J. Cell. Mol. Med.* 13(8b):1792-1808, 2009.
Polster et al., "BH3 Death Domain Peptide Induces Cell Type-selective Mitochondrial Outer Membrane Permeability," *The Journal of Biological Chemistry* 276:37887-37894, 2001.
Presta, "Antibody engineering," *Curr. Op. Struct. Biol.* 2:593-596, 1992.
Pritzker, "Cancer Biomarkers: Easier Said Than Done," *Clinical Chemistry* 48:1147-1150, 2002.
Putcha et al., *Neuron* 29(3):615-628, 2001.
Puthalakath et al., "The Proapoptotic Activity of the Bcl-2 Family Member Bim is Regulated by Interaction with the Dynein Motor Complex," *Mol. Cell.* 3:287-296, 1999.
Puthalakath et al., "Bmf: A Proapoptotic BH3-Only Protein Regulated by Interaction with the Myosin V Actin Motor Complex, Activated by Anoikis," *Science* 293:1829-1832, 2001.
Puthalakath et al., "Keeping killers on a tight leash: transcriptional and post-translational control of the pro-apoptotic activity of BH3-only proteins," *Cell Death Differ.* 9:505-512, 2002.
Quinsay et al., "Proapoptotic Bnip3 Mediates Permeabilization of Mitochondria and Release of Cytochrome c via a Novel Mechanism," *Circulation* 118(18): Supply 2, S388, 2008—Abstract.
Raff, "Social controls on cell survival and cell death," *Nature* 356:397-400, 1992.
Rassenti et al., "ZAP-70 Compared with Immunoglobulin Heavy-Chain Gene Mutation Status as a predictor of Disease Progression in Chronic Lymphocytic Leukemia," *N. Engl. J. Med.* 351:893-901, 2004.
Ravandi et al., "Evaluating measurable residual disease in acute myeloid leukemia," *Blood Adv.* 2(11): 1356-1366, 2018.
Ray et al., "BNIP3 Heterodimerizes with Bcl-2/Bcl-xl and Induces Cell Death Independent of a Bcl-2 Homology 3 (BH3) Domain at Both Mitochondrial and Nonmitochondrial Sites," *J. Biol. Chem.* 275(2):1439-1448, 2000.
U.S. National Library of Medicine, "A Phase 1 Study Evaluating CPI-0610 in Patients with Progressive Lymphoma", ClinicalTrials.gov, Identifier, NCT01949883 First Posted Sep. 24, 2013, Last Update Posted Sep. 26, 2013, retrieved from https://clinicaltrials.gov/ct2/history/NCT01949883?a=2&b=2&c=merged#StudyPageTop, 7 pages.
Besbes, S. and Billard, C., "First MCL-1-Selective BH3 Mimetics as Potential Therapeutics for Targeted Treatment of Cancer", Cell Death and Disease, 6:2 pages (2015).
Clinical Study, No Authors Available, "Alvocidib, Followed by Cytarabine + Mitoxantrone, Makes Impact in AML", Inpharma Weekley, 1606:8 (2007).
Hewings et al., "Optimization of 3,5-Dimethylisoxazole Derivatives as Potent Bromodomain Ligands" *J. Med. Chem.*, 56:3217-3227, 2013.
Itzykson, R. and Fenaux, P., "Predicting the Outcome of Pateients with Higher-Risk Myelodysplastic Syndrome Treated with Hypomethylating Agents", Leukemia & Lymphoma, 53(5):760-762 (2012).
Ji, et al., "A Pharmacokinetic/Pharmacodynamic Model of Tumor Lysis Syndrome in Chronic Lynphocytic Leukemia Patients Treated with Flaovpiridol", Clinical Cancer Research, 19(5):1269-1280 (2013).
Kim, et al., "TP-1287, an oral prodrug of the cyclin-dependent kinase-9 inhibitor alvocidib", EHA Library Jun. 9, 2016. Retrieved

(56) References Cited

OTHER PUBLICATIONS on Jan. 24, 2020 URL:https://library.ehaweb.org/eha/2016/21st/132440/clifford.whatcott.tp-1287.prodrug.of.the.cyclin-dependent.kinase-9.htm; poster.

Qi, et al., "A Subset of Small Cell Lunng Cancer (SCLC) Cell Lines is MCL-1-Dependent and Responds to Cyclin-Dependent Kinase (CDK)9 Inhibition in vitro and in vivo", Cancer Research, 72(8): Suppl. 1, Abstract 2016, 4 pages, (2012).

Smith, D. B., et al, "An Alvocidib-Containing Regimen is Highly Effective in AML Patients Through a Mechanism Dependent on MCL1 Expression and Function," J. Clin. Oncol, 33: abstract 7062, 3 pages (2015).

Stephens, D.M., et. al., "Cyclophosphamide, Alvocidib (Flavorpiridol), and Rituximab, a Novel Feasible Chemoimmunotherapy Regimen for Patients with High-Risk Chronic Lymphocytic Leukemia", Leukemia Research, 37:1195-1199 (2013).

Tan, et al., "The DNA Methyltransferase Inhibitor Zebularine Induces Mitochondria-Mediated Apoptosis in Gastric Cells in Vitro and in Vivo", Biochemical and Biophysical Research Communications, 430:250-255 (2013).

U.S. National Library of Medicine, "Alvocidib, Cytarabine, and Mitoxantrone in Treating Patients with Newly Diagnosed Acute Myeloid Leukemia", ClinicalTrials.gov Identifier: NCT00795002 First Posted Nov. 21, 2008, Last Update Posted Aug. 7, 2018, retrieved from https://clinicaltrials.gov/ct2/show/NCT00795002, 11 pages.

Zeidner, et al., "Randomized Phase II Trial of Timed-Sequential Therapy (TST) with Flavopirodol (Alvocidib), Ara-C and Mitoxantrone (FLAM) Versus "7+3" for Adults Ages 70 Year and Under with Newly Diagnosed Acute Myeloid Leukemia (AML)", Blood, 120(21):Abstract 47; 5 pages (2012).

\* cited by examiner

Alvocidib+Aza normalized to Alvocidib only treatment

COMBINATION THERAPIES FOR TREATMENT OF CANCER

This application is a continuation of U.S. Ser. No. 16/665,277 filed Oct. 28, 2019, allowed, which is a continuation of U.S. Ser. No. 15/750,151 filed Feb. 2, 2018, which is a 371 application of PCT/US2016/045423, filed Aug. 3, 2016, and claims benefit of provisional application 62/200,499 filed Aug. 3, 2015. The contents of each of these applications are incorporated herein by reference in their entirety.

BACKGROUND

Technical Field

The present invention is generally directed to methods for treatment of cancer by administration of a cyclin-dependent kinase inhibitor and a DNA methyltransferase inhibitor.

Description of the Related Art

Myelodysplastic Syndrome (MDS) is a diverse group of bone marrow disorders characterized by the inability to produce healthy numbers of blood cells. Frequently (around 30%) MDS progresses to acute myelogenous leukemia (AML), which remains largely an incurable condition with relatively poor survival rates. One treatment option for MDS is the hypomethylating agents azacitidine and deoxyazacitidine (decitabine), which act by 2 principle mechanisms: 1) inhibiting DNA methyltransfereases, which leads to the activation of key tumor suppressor genes; and 2) directly damaging DNA following incorporation in replicating DNA strands. The second of these mechanisms activates the programmed cell-death pathway (apoptosis), and this pathway has been shown to depend somewhat on the expression levels of key apoptosis regulatory proteins, including MCL-1, an anti-apoptotic member of the BH3 family of apoptotic regulating proteins.

Cyclin-dependent kinases (CDKs) are important regulators that control the timing and coordination of the cell cycle. CDKs form reversible complexes with their obligate cyclin partners to control transition through key junctures in the cell cycle. In addition to regulating cell cycle progression, some CDK family members also play an active role in transcription, for example CDK7 and CDK9. In particular, CDK9 directly phosphorylates RNA Polymerase II and contributes towards productive transcription. Agents which inhibit CDK9 have been shown to inhibit the expression of MCL-1, an important protein in the apoptosis pathway activated by DNA methyltransferase inhibitors. One such CDK inhibitor is alvocidib, which is a potent and selective inhibitor of the CDKs (e.g., CDK-9) and has antitumor activity against various tumor cells lines. Alvocidib is also known to rapidly decrease expression levels of MCL-1.

To date, there have been no reports of combinations of DNA methyltransferase inhibitors and cyclin-dependent kinase inhibitors for treatment of cancers, such as MDS and/or AML. While progress has been made, there remains a need in the art for improved combination therapies for treatment of various cancers. The present invention fulfills this need and provides related advantages.

BRIEF SUMMARY

In brief, embodiments of the present invention provide methods for treatment of cancer comprising administration of two different therapeutic agents. In one embodiment the disclosure provides a method for treating cancer in a mammal in need thereof, the method comprising administering to the mammal an effective amount of the following therapeutic agents:

i) a cyclin-dependent kinase inhibitor, and
ii) a DNA methyltransferase inhibitor.

Kits comprising a cyclin-dependent kinase inhibitor, a DNA methyltransferase inhibitor, and instructions for administering the cyclin-dependent kinase inhibitor and the DNA methyltransferase inhibitor to a mammal in need of treatment for cancer, as well as pharmaceutical compositions useful in the disclosed methods, are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1A:
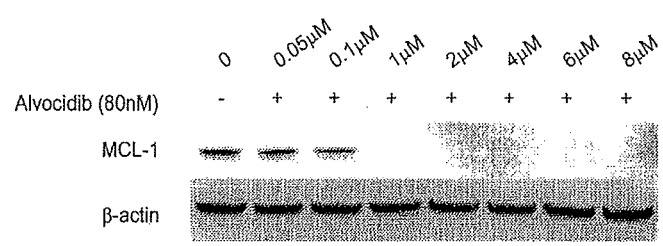
FIG. 1A provides relative expression levels of MCL-1 compared to β-actin in MV 4-11 cells across a range of alvocidib doses.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

A "DNA methyltransferase inhibitor" is an agent having dual activity as an inhibitor of DNA methyltransferase (i.e., a hypomethylating agent) and activity as a DNA-damaging agent. Exemplary DNA methyltransferase inhibitors are incorporated into DNA (e.g., DNA in a cancer cell), thereby inhibiting DNA methyltransferase and leading to DNA damage and apoptosis. Exemplary DNA methyltransferase inhibitors include nucleoside analogues, such as azanucleosides.

A "cyclin-dependent kinase inhibitor" is an agent which inhibits the activity of cyclin dependent kinases (CDKs), including CDK1, CDK2, CDK3, CDK4, CDK5, CDK6, CDK7, CDK8, CDK9 and CDK11. Exemplary CDK inhibitors inhibit the expression of MCL-1. Exemplary CDK inhibitors include, but are not limited to, alvocidib, dinaciclib, olomoucine, roscovitine, purvalanol, paullones, palbociclib, thio/oxoflavopiridols, oxindoles, aminothiazoles, benzocarbazoles, pyrimidines and seliciclib.

"Alvoeidib" (also known as "Flavopiridol") is a synthetic flavone having the following structure:

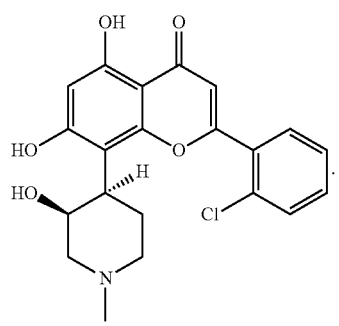

"Azanucleosides" are analogues of natural occurring nucleosides, wherein at least one carbon atom has been replaced with a nitrogen atom. Exemplary azanucleosides include azacitidine and decitabine, which have the following structures, respectively:

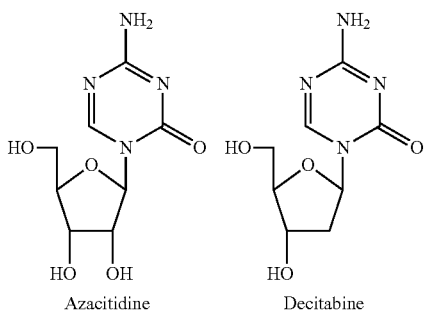

"Mammal" includes humans and both domestic animals such as laboratory animals and household pets (e.g., cats, dogs, swine, cattle, sheep, goats, horses, rabbits), and non-domestic animals such as wildlife and the like.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment, as defined below, of a cancer in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having cancer, disease, or condition of interest, and includes:

(i) preventing the cancer, disease, or condition from occurring in a mammal, in particular, when such mammal is predisposed to the condition but has not yet been diagnosed as having it;

(ii) inhibiting the cancer, disease, or condition, i.e., arresting its development;

(iii) relieving the cancer, disease, or condition, i.e., causing regression of the disease or condition; or (iv) relieving the symptoms resulting from the cancer, disease, or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

I. Methods

In certain embodiments, the methods are useful for treating cancer cells and/or for preventing, treating, or ameliorating a cancer and/or symptoms thereof, in a mammal, preferably a human. Accordingly, in one embodiment the disclosure provides a method for treating a cancer in a mammal in need thereof, the method comprising administering to the mammal a therapeutically effective amount of the following therapeutic agents:

i) a cyclin-dependent kinase inhibitor, and
ii) a DNA methyltransferase inhibitor.

In certain embodiments, the cyclin-dependent kinase inhibitor inhibits cyclin-dependent kinase (Cdk) proteins, such as Cdk4, Cdk6, Cdk7, Cdk8, Cdk9, Cdk10 and/or Cdk11. In some embodiments, the cyclin-dependent kinase inhibitor inhibits Cdk7, Cdk9 or both. In other embodiments, the cyclin dependent kinase inhibitor inhibits expression of MCL-1. In some embodiments, the cyclin-dependent kinase inhibitor is alvociclib or dinaciclib or a pharmaceutically acceptable salt thereof. For example, in some more specific embodiments the cyclin-dependent kinase inhibitor is alvocidib or a pharmaceutically acceptable salt thereof. In some other specific embodiments the cyclin-dependent kinase inhibitor is dinaciclib or a pharmaceutically acceptable salt thereof.

In some embodiments, the DNA methyltransferase is capable of being incorporated into RNA and/or DNA. In other embodiments, the DNA methyltransferase inhibitor activates apoptosis due to DNA damage. In still different embodiments, the DNA methyltransferase inhibitor is a nucleoside analogue. In more embodiments, the DNA methyltransferase inhibitor is an azanucleoside, such as azacitidine or decitabine a pharmaceutically acceptable salt thereof. In some more specific embodiments, the DNA methyltransferase inhibitor is azacitidine or a pharmaceutically acceptable salt thereof. In some other embodiments, the DNA methyltransferase inhibitor is decitabine or a pharmaceutically acceptable salt thereof.

In further embodiments of the foregoing, the cyclin-dependent kinase inhibitor is alvocidib, or a pharmaceutically acceptable salt thereof, and the DNA methyltransferase inhibitor is azacitidine or a pharmaceutically acceptable salt thereof. In other different embodiments, the cyclin-dependent kinase inhibitor is alvocidib, or a pharmaceutically acceptable salt thereof, and the DNA methyltransferase inhibitor is decitabine or a pharmaceutically acceptable salt thereof.

The cyclin-dependent kinase inhibitor and the DNA methyltransferase inhibitor can be co-administered or administered sequentially. For example, in some embodiments the cyclin-dependent kinase inhibitor is administered and after a sufficient period of time the DNA methyltransferase inhibitor is administered. In some other embodiments the DNA methyltransferase inhibitor is administered and after a sufficient period of time the cyclin-dependent kinase inhibitor is administered. One of ordinary skill in the art can derive an appropriate dosing schedule based on common techniques and knowledge.

In some embodiments, the cyclin-dependent kinase inhibitor is administered to the mammal prior to administration of the DNA methyltransferase inhibitor. For example in some embodiments, the DNA methyltransferase inhibitor is administered within about 24 to 48 hours after administration of the cyclin-dependent kinase inhibitor. In some other embodiments, the DNA methyltransferase inhibitor is administered to the mammal prior to administration of the cyclin-dependent kinase inhibitor.

A wide variety of cancers, including solid tumors and leukemias (e.g., acute myeloid leukemia) are amenable to the methods disclosed herein. Types of cancer that may be treated in various embodiments include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include, but are not limited to, angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In certain more specific embodiments, the cancer is a hematologic cancer. For example, in some embodiments the hematologic cancer is selected from acute myelogenous leukemia (AIVIL), multiple myeloma, follicular lymphoma, acute lymphoblastic leukemia (ALL), chronic lymphocytic leukemia (CLL) and non-Hodgkin's lymphoma. In other embodiments, the hematological cancer is acute myelogenous leukemia (AML). In some more embodiments, the hematologic cancer is myelodysplastic syndrome (MDS).

II. Kits and Pharmaceutical Compositions

Other embodiments are directed to kits useful for implementation of the disclosed methods. For example, in some embodiments is provided a kit comprising a cyclin-dependent kinase inhibitor, a DNA methyltransferase inhibitor, and instructions for administering the cyclin-dependent kinase inhibitor and the DNA methyltransferase inhibitor to a mammal in need of treatment for cancer. In some embodiments, the cyclin-dependent kinase inhibitor present in the kit is as defined in any one of the foregoing embodiments. In other embodiments, the DNA methyltransferase inhibitor which is part of the kit is as defined in any of the foregoing embodiments. In still more embodiments, the cancer treatable with the kits is as defined in any one of the foregoing embodiments.

In other embodiments pharmaceutical compositions are provided. For example, in some embodiments the pharmaceutical composition comprises a pharmaceutically acceptable carrier or excipient and the following therapeutic agents:

i) a cyclin-dependent kinase inhibitor, and
ii) a DNA methyltransferase inhibitor.

The therapeutic agents present in the pharmaceutical compositions may be any of those described herein or known in the art. In some embodiments, the composition comprises alvocidib. In some other embodiments, the composition comprises azacitidine. In some embodiments, the composition comprises decitabine. In some other embodiments the pharmaceutical composition comprises a pharmaceutically acceptable carder or excipient, alvocidib and azacitidine. In different embodiments the pharmaceutical composition comprises a pharmaceutically acceptable carrier or excipient, alvocidib and decitabine.

In some embodiments, the pharmaceutical composition is formulated for oral administration. In other embodiments, the pharmaceutical composition is formulated for injection.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, one or more of the compounds as described herein (i.e., a cyclin dependent kinase inhibitor and/or a DNA methyltransferase inhibitor, referred to herein as "the compounds") are administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the one or more of the compounds are delivered in a targeted drug delivery system, for example, in a liposome coated with organ-specific antibody. In such embodiments, the liposomes are targeted to and taken up selectively by the organ. In yet other embodiments, one or more of the compounds are provided in the form of a rapid release formulation, in the form of an extended release formulation, or in the form of an intermediate release formulation. In yet other embodiments, one or more of the compounds are administered topically.

The compounds are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, one or more of the compounds are administered in a single dose. Typically, such administration will be by injection, e.g., intravenous injection, in order to introduce the agent quickly. However, other routes are used as appropriate. A single dose of the compounds may also be used for treatment of an acute condition.

In some embodiments, one or more of the compounds are administered in multiple doses. In some embodiments, dosing is about once, twice, three times, four times, five times, six times, or more than six times per day. In other embodiments, dosing is about once a month, once every two weeks, once a week, or once every other day. In another embodiment the compounds are administered together about once per day to about 6 times per day. In another embodiment the administration of the compounds continues for less than about 7 days. In yet another embodiment the administration continues for more than about 6, 10, 14, 28 days, two months, six months, or one year. In some cases, continuous dosing is achieved and maintained as long as necessary.

Administration of the compounds may continue as long as necessary. In some embodiments, the compounds are administered for more than 1, 2, 3, 4, 5, 6, 7, 14, or 28 days. In some embodiments, the compounds are administered for less than 28, 14, 7, 6, 5, 4, 3, 2, or 1 day. In some embodiments, the compounds are administered chronically on an ongoing basis, e.g., for the treatment of chronic effects.

In some embodiments, the compounds are administered in dosages. Due to intersubject variability in compound pharmacokinetics, individualization of dosing regimen is provided in certain embodiments. Dosing for the compounds may be found by routine experimentation in light of the instant disclosure and/or can be derived by one of ordinary skill in the art.

In some embodiments, the compounds are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

A pharmaceutical composition, as used herein, refers to a mixture of one or more of the compounds with other chemical components, such as carriers, stabilizers, In diluents, dispersing agents, suspending agents, thickening agents, and/or excipients. In certain embodiments, the pharmaceutical composition facilitates administration of the compounds to an organism. In some embodiments, practicing the methods of treatment or use provided herein, therapeutically effective amounts cyclin-dependent kinase and/or DNA methyltransferase inhibitors provided herein are administered in a pharmaceutical composition to a mammal having a cancer, disease, disorder, or medical condition to be treated. In specific embodiments, the mammal is a human. In certain embodiments, therapeutically effective amounts vary depending on the severity of the cancer, disease, the age and relative health of the subject, the potency of the compound used, and other factors. The compounds are used in combination with each other or as components of mixtures.

In one embodiment, cyclin-dependent kinase inhibitor and/or DNA methyltransferase inhibitor components are formulated in an aqueous solution. In specific embodiments, the aqueous solution is selected from, by way of example only, a physiologically compatible buffer, such as Hank's solution, Ringer's solution, or physiological saline buffer. In other embodiments, cyclin-dependent kinase inhibitors and/or DNA methyltransferase inhibitors are formulated for transmucosal administration. In specific embodiments, transmucosal formulations include penetrants that are appropriate to the barrier to be permeated. In still other embodiments wherein the compounds are formulated for other parenteral injections; appropriate formulations include aqueous or nonaqueous solutions. In specific embodiments, such solutions include physiologically compatible buffers and/or excipients.

In another embodiment, the compounds are formulated for oral administration. The compounds are formulated by combining the compounds with, e.g., pharmaceutically acceptable carriers or excipients. In various embodiments, the compounds are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethyleellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of compound doses.

In certain embodiments, therapeutically effective amounts of the compounds are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of the compounds are formulated for buccal or sublingual administration. Formulations suitable for buccal or sublingual administration include, by way of example only, tablets, lozenges, or gels. In still other embodiments, the compounds are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, therapeutically effective amounts of the compounds are administered topically. In some embodiments, the compounds are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, therapeutically effective amounts of the compounds are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of therapeutically effective amounts of the compounds is accomplished by means of iontophoretic patches and the like. In certain embodiments, transdermal patches provide controlled delivery of therapeutically effective amounts of compounds described herein. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, therapeutically effective amounts of the compounds are formulated for administration by inhalation. Various forms suitable for administration by inhalation include, but are not limited to, aerosols, mists or powders. Pharmaceutical compositions of therapeutically effective amounts of the compounds are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator is formulated containing a powder mix of the compound and a suitable powder base such as lactose or starch.

In still other embodiments, therapeutically effective amounts of the compounds are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the compounds into preparations which can be used pharmaceutically. Proper formulation is dependent upon the route of administration chosen. Any pharmaceutically acceptable techniques, carriers, and excipients are optionally used as suitable. Pharmaceutical compositions comprising inhibitors targeting at least two super-enhancer components are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and therapeutically effective amounts of one or more of the compounds as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds are included within the scope of the compounds presented herein. Additionally, the compounds encompass unsolvated as well as solvated forms with pharmaceutically acceptable solvents such as water, ethanol, and the like. The solvated forms of therapeutically effective amounts of the compounds are also considered to be disclosed herein, In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising therapeutically effective amounts of the compounds include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising therapeutically effective amounts of compounds described herein illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix, In some embodiments, a liquid composition includes a gel formulation, In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid solubility of therapeutically effective amounts of compounds described herein. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more of the compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of the one or more compounds is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more the one or more compounds is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of the one or more compounds is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the one or more compounds is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of the one or more compounds is in the range of 0.0001-10 g, 0.0005-9 g, 0.001-8 g, 0.005-7 g, 0.01-6 g, 0.05-5 g, 0.1-4 g, 0.5-4 g, or 1-3 g.

EXAMPLES

Example 1

Alvocidib Lowers MCL-1 Expression in a Time and Dose Dependent Manner

An AML cell line, MV-4-11, expresses MCL-1. MCL-1 is a key anti-apoptotic protein in MV-4-11 cells. Alvocidib, a CDK9 inhibitor, lowers the expression of MCL-1, which is already well documented in the literature. Alvocidib down-regulates MCL-1 in a dose dependent manner (FIG. 1A). The dose dependence is observed by monitoring the relative expression of MCL-1 compared to β-actin when cells are dosed with alvocidib at concentrations of 0-8 µM. MV4-11 cells were treated with Alvocidib for 16 hrs in vitro, Following treatment, cells were harvested and prepared using standard western blotting technique for immuno-detection of MCL-1 and β-actin expression. Dosage of 0.1 µM Alvocidib reduced MCL-1 expression, whereas 1 µM Alvocidib completely blocked expression at 16 hrs.

Figure 1B:
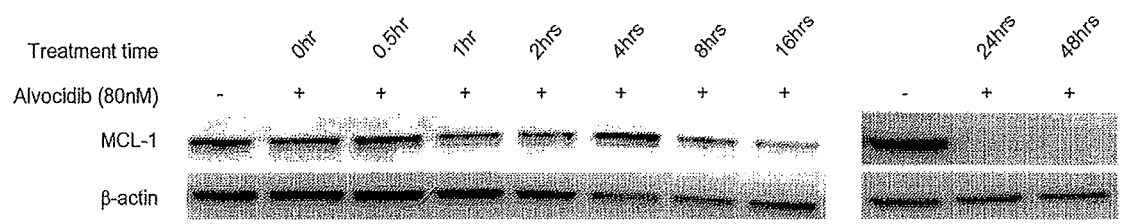
FIG. 1B is a gel showing relative expression levels of MCL-1 compared to β-actin in MV 4-11 cells across a range of time points.

In addition, alvocidib also down-regulates MCL-1 in a time-dependent manner (FIG. 1B). The time dependence is observed by monitoring the relative expression of MCL-1 compared top-actin over time. The relative expression of MCL-1 was measured at 0.5-48 hour time points after dosing with 80 nM of alvocidib.

MV4-11 cells were treated with 80 nM Alvocidib in vitro for the times indicated. Following treatment, cells were harvested and prepared using standard western blotting technique for immunodetection of MCL-1 and β-actin expression. Alvocidib reduced MCL-1 expression as early as 1 hour post-treatment, whereas MCL-1 expression was nearly completely blocked at 16 hrs. This inhibition of expression was maintained for up to 48 hours following treatment. The relative expression of MCL-1 shows that alvocidib lowers the expression of MCL-1 in MV 4-11 cells.

Example 2

Combination Treatment with Alvocidib and Azacitidine and its Effect on Cell Viability AML cell proliferation is inhibited synergistically by dosing with alvocidib and azacitidine. Alvocidib was used alone and in combination with azacitidine in order to determine the effect of the single drug and combination on cell viability. A significant shift in cell viability was observed when cells were dosed with the combination of alvocidib and azacitidine compared with cells dosed only with azacitidine.

Figure 2:
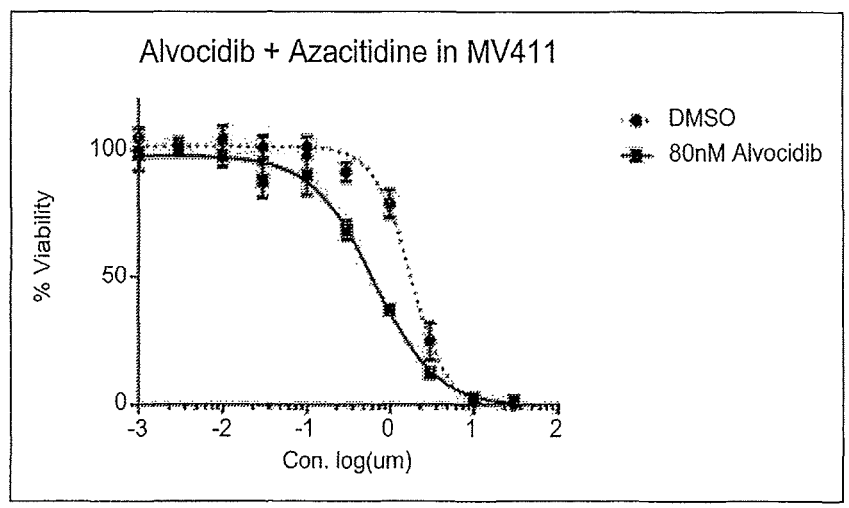
FIG. 2 is a graph of cell showing the synergistic effect of combining alvocidib with azacitidine to inhibit MV 4-11 cell growth.

MV 4-11 cells were dosed first with alvocidib (80 nM) or DMSO for 24 hours followed by a wash step. Following the wash step, the cells were dosed with azacitidine (30 μM to 0.001 μM) for an additional 72 hours, Measurement of cell viability was taken at 96 hours from the initial dose (72 hours after the wash step) and normalized to data collected for cells dosed with alvocidib only. Cell viability was then assessed in a Cell titer-glo assay, according to manufacturer protocol. Cell viability was then plotted against concentration on a logarithmic scale (FIG. 2). The addition of 80 nM Alvocidib results in a left shift of the IC50 curve, when normalized to the Alvocidib-only treatment, indicating synergistic activity in 5-Azacytidine efficacy with the combination. The resultant EC50 was lowered from 1.779 μM for cells dosed with only azacitidine compared to 0.6408 μM for cells also dosed with alvocidib.

These results provide evidence for increased activity (e.g., synergy) for a combination of alvocidib and azacitidine relative to the single agents.

Example 3

Combination Treatment, Effect on Caspase 3/7 Activity and Apoptosis

Alvocidib was used combination with azacitidine to treat MV 4-11 cells. The combination treatment was compared with treatment using azacitidine only. The comparison was used to assess the synergistic effect of the combination on caspase 3/7 activity and apoptosis. The addition of 80 nM Alvocidib to 5-Azacytidine treatment results in synergistic increases in caspase activity in MV4-11 cells.

Figure 3:
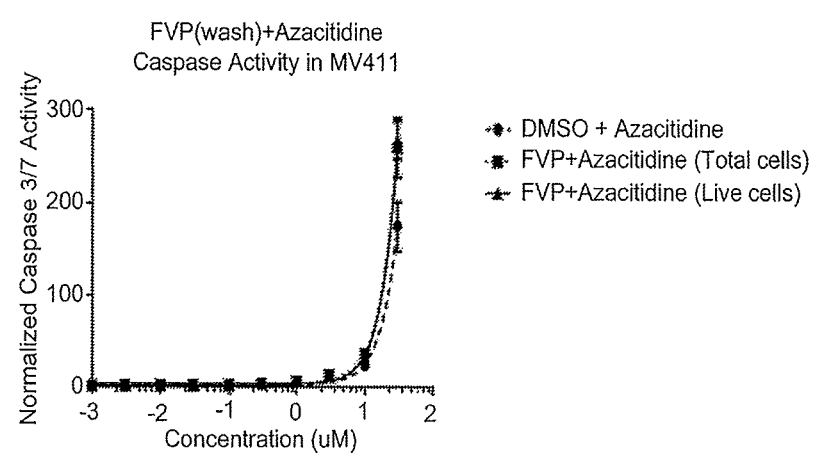
FIG. 3 present caspase 3/7 activity compared with concentration on a logarithmic scale for combinations of alvocidib with azacitidine to induce apoptosis in MV 4-11 cells.
Figure 4A:
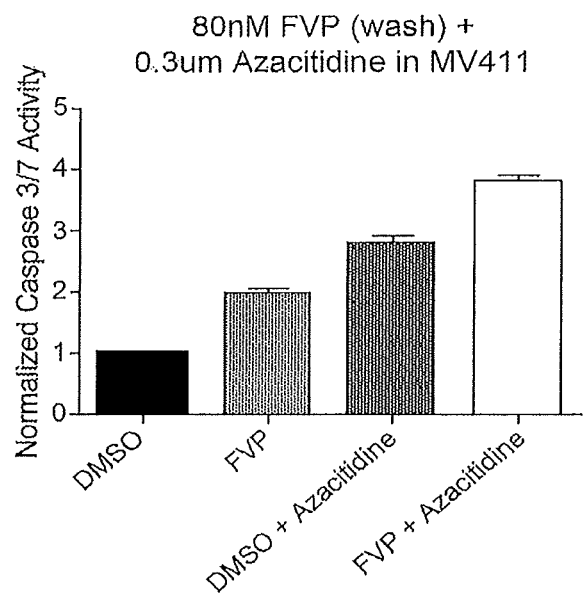
FIGS. 4A-D are bar graphs providing data for treatment of MV 4-11 cells with alvocidib or azacitidine alone, or in combination, at various concentrations of azacitidine.
Figure 4B:
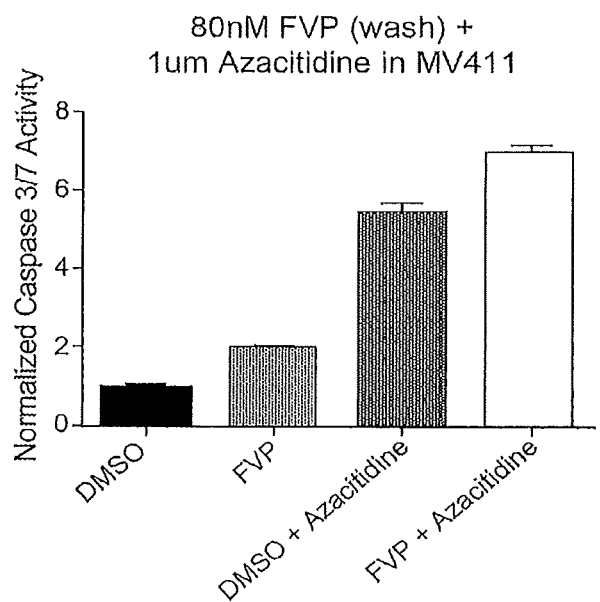
Figure 4C:
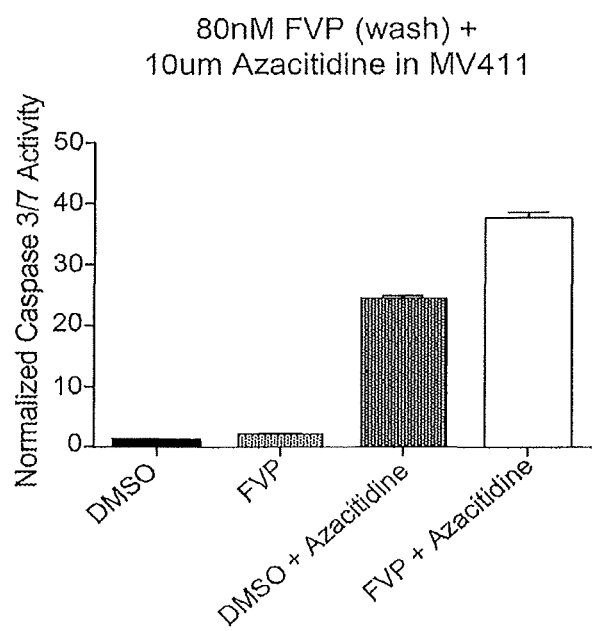
Figure 4D:
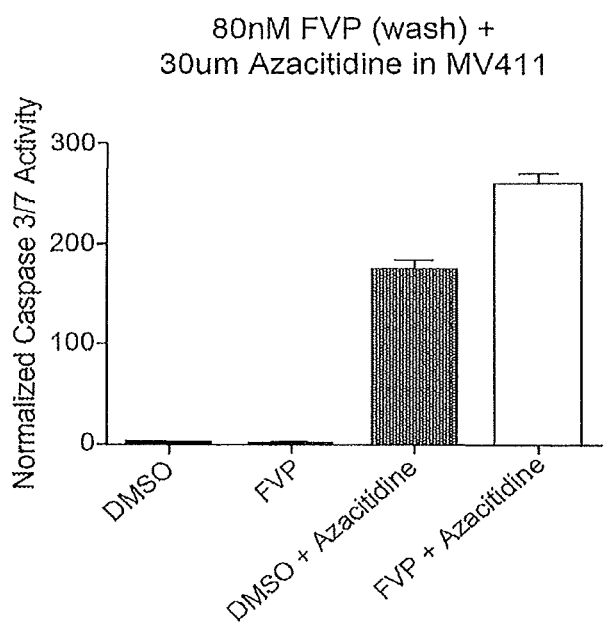

The cells were dosed initially with alvocidib for 24 hours followed by a wash step. Next, cells were dosed with azacitidine for 24 hours. Caspase 3/7 activity was measured 48 hours after the initial dose of alvocidib (24 hours after wash step and dose of azacitidine). The normalized caspase 3/7 activity of cells treated with the combination of alvocidib (FVP) and azacitidine was plotted against the concentration range of azacitidine (see FIG. 3). The dose of alvocidib remained constant (80 nM) across the dosing range for azacitidine (0.3 μM-30 μM). Apoptosis was then assessed in a Caspase-glo assay, according to manufacturer protocol.

In order to measure the synergistic effect of the combination of alvocidib and azacitidine, the caspase 3/7 activity for untreated cells was plotted with cells treated with a single agent and a combination of alvocidib and azacitidine. The cells treated with a single agent were treated with either alvocidib (80 nM) or azacitidine+DMSO (0.3 μM-30 μM) for 48 hours. The cells treated with a combination of alvocidib and azacitidine were initially treated with alvocidib (80 nM) for 24 hours. The cells were then washed and treated with azacitidine (0.3 μM-30 μM) for 24 hours. Results for different concentrations of azacitidine are provided in FIGS. 4A-4D. The comparisons show that at the tested concentrations of azacitidine and alvocidib the combination schedule gives rise to a synergistic increase in caspase 3/7 activity/apoptosis compared to untreated cells or cells treated with either agent alone.

Example 4

Figure 5A:
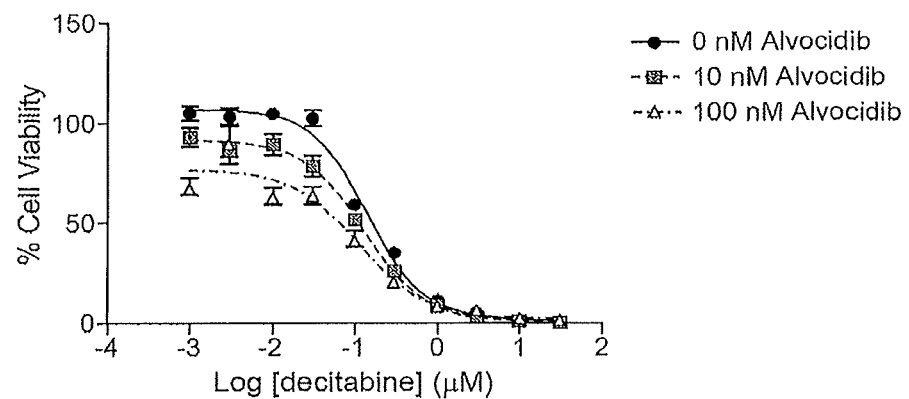
FIGS. 5A and 5B present data from combination treatment of alvocidib and decitabine in MV4-11 cells.
Figure 5B:
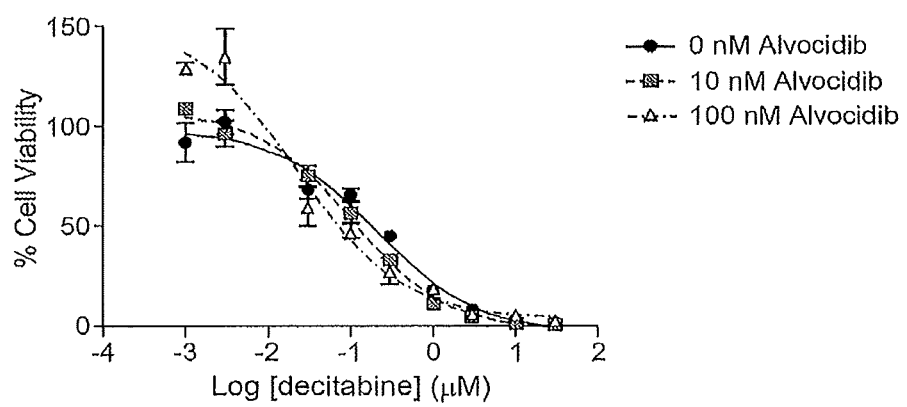

Combination Treatment with Alvocidib and Decitabine and its Effect on Cell Viability FIGS. 5A and 5B present data from combination treatment of Alvocidib and decitabine in MV4-11 cells. MV4-11 cells were first treated for 96 hours with alvocidib+decitabine according to the general procedures of Example 2 at the concentrations indicated in FIG. 5A. A modest reduction in the IC50 (μM) was observed with the addition of alvocidib, Alternatively, MV4-11 cells were pre-treated for 24 hours with alvocidib, then treated for an additional 72 hours with decitabine (96 hours total, FIG. 5B). Here, a change of nearly 10-fold in the IC50 (μM) of decitabine with the addition of alvocidib (100 nM) was observed when alvocidib was administered prior to decitabine.

All of the U.S. patents, specifically U.S. Patent Application No. 62/200,499, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method of treating a subject with myelodysplastic syndrome (MDS) comprising treating the subject with a therapeutically effective amount of at least one of decitabine or azacitidine and a therapeutically effective amount of alvocidib.

2. The method of claim 1 comprising treating the subject with a therapeutically effective amount of decitabine and a therapeutically effective amount of alvocidib.

3. The method of claim 1 comprising treating the subject with a therapeutically effective amount azacitidine and a therapeutically effective amount of alvocidib.

4. A method of treating a subject with myelodysplastic syndrome (MDS) comprising administering to the subject with a therapeutically effective amount of at least one of decitabine or azacitidine and a therapeutically effective amount of alvocidib.

5. The method of claim 4 comprising administering to the subject a therapeutically effective amount of decitabine and a therapeutically effective amount of alvocidib.

6. The method of claim 4 comprising administering the subject a therapeutically effective amount azacitidine and a therapeutically effective amount of alvocidib.

* * * * *